US007501557B1

(12) United States Patent
Wagner et al.

(10) Patent No.: US 7,501,557 B1
(45) Date of Patent: Mar. 10, 2009

(54) METHOD UTILIZING THE TOBACCO PHYLLOPLANIN PROMOTER FOR EXPRESSION OF NUCLEIC ACIDS AS GENE PRODUCTS DIRECTED TO AERIAL SURFACES OF PLANTS

(75) Inventors: George J. Wagner, Wilmore, KY (US); Ryan W. Sheperd, Berkeley, CA (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/680,051

(22) Filed: Feb. 28, 2007

Related U.S. Application Data

(60) Provisional application No. 60/777,383, filed on Feb. 28, 2006.

(51) Int. Cl.
*C12N 15/82* (2006.01)
*C07H 21/04* (2006.01)

(52) U.S. Cl. ....................... 800/287; 800/288; 435/468; 536/24.1

(58) Field of Classification Search ....................... None
See application file for complete search history.

(56) References Cited

U.S. PATENT DOCUMENTS 6,541,682 B1 * 4/2003 Nehra et al. ................ 800/278

OTHER PUBLICATIONS

PubMed Search Results; "phylloplanin"; p. 1 of 1.*
Shepherd et al. *Nicotiana tabacum* phylloplanin gene, phylloplanin precursor, gene, complete cds. (2005) GenBank Accession AY705384; pp. 1-2.*
Shepherd et al. Phylloplanins of tobacco are defensive proteins deployed on aerial surfaces by short glandular trichomes. (2005) The Plant Cell; "Preview", pp. 1-11.*
Larkin et al . Arabidopsis GLABROUS1 gene requires downstream sequences for function. (1993) The Plant Cell; vol. 5, pp. 1739-1748.*
Akers et al. (1978). Ultrastructure of glandular trichomes of leaves of *nicotiana tabacum l.*, cv Xanthi. American Journal of Botany 65:3, 282-292.
Curstedt et al. (1987). Two hydrophobic low-molecular-mass protein fractions of pulmonary surfactant: characterization and biophysical activity. Eur. J. Biochem. 168, 255-262.
Gallo et al. (1998). Antimicrobial peptides: an emerging concept in cutaneous biology. J. Invest. Dermatol. 111, 739-743.
Horsch et al. (1985). A simple and general method for transferring genes into plants. Science 227, 1229-1231.
Kandra et al. (1990). Modified branched-chain amino acid pathways give rise to acyl acids of sucrose esters exuded from tobacco leaf trichomes. Eur. J. Biochem. 188, 385-391.
Kowalski et al. (1992). Purification and characterization of polyphenol oxidase from glandular trichomes of *solanum berthaultii*. Plant Physiol. 100, 677-684.
Matsudaira, P. (1987). Sequence from picomole quantities of proteins electroblotted onto polyvinylidene difluoride membranes. J. Biol. Chem. 262:21, 10035-10038.
Page, R.D.M. (1996) TreeView: an application to display phylogenetic trees on personal computers. Comp. Appl. Biosci. 12:4, 357-358.
Reuveni et al. (1987). Removal of duvatrienediols from the surface of tobacco leaves increases their susceptibility to blue mold. Physiological and Molecular Plant Pathology 30, 411-451.
Samac et al. (1991). Developmental and pathogen-induced activation of the Arabidopsis acidic chitinase promoter. The Plant Cell 3, 1063-1072.
Schroder, J.-M. (1999). Epithelial antimicrobial peptides: innate local host response elements. Cell. Mol. Life Sci. 56, 32-46.
Terry et al. (1980). An examination of centrifugation as a method of extracting an extracellular solution from peas, and its use for the study of indoleacetic acid-induced growth. Plant Physiol. 66, 321-325.
Wagner et al. (2004). New approaches for studying and exploiting an old protuberance, the plant trichome. Annals of Botany 93, 3-11.
Wang et al. (2001). Suppression of a P450 hydroxylase gene in plant trichome glands enhances natural-product-based aphid resistance. Nat. Biotechnol. 19, 371-374.
Weaver et al. (2001). Functions of surfactant proteins B and C. Annu. Rev. Physiol. 63, 555-578.

* cited by examiner

*Primary Examiner*—Cathy Kingdon Worley
(74) *Attorney, Agent, or Firm*—Stites & Harbison PLLC; Stephen Weyer; Richard S. Myers, Jr.

(57) ABSTRACT

A method and system is provided for generating excreted gene products in a plant which includes generating a nucleic acid fusion construct comprising a phylloplanin promoter and a selected non-phylloplanin nucleic acid sequence whose transcription product is to be expressed and delivered to an aerial surface of a plant. The method includes transfecting plant cells with the nucleic acid fusion construct and allowing the plant cells to express the non-phylloplanin nucleic acid sequence transcription product which is then excreted from the plant cells to the aerial surfaces.

9 Claims, 14 Drawing Sheets

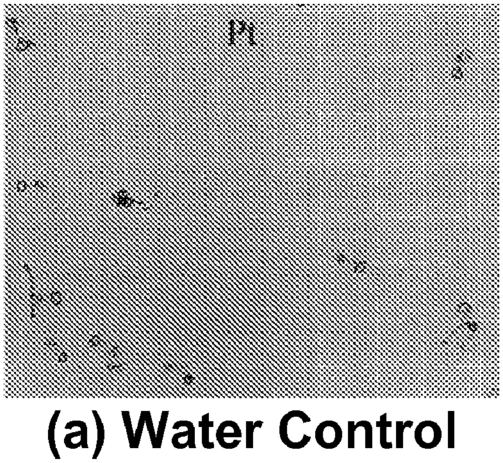
(a) Water Control
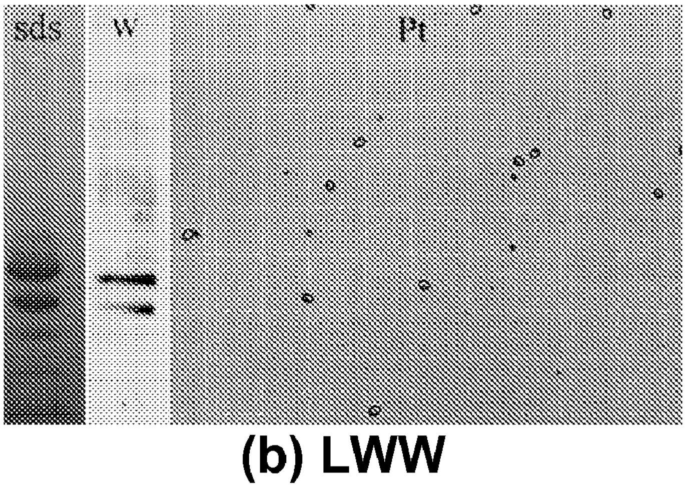
(b) LWW
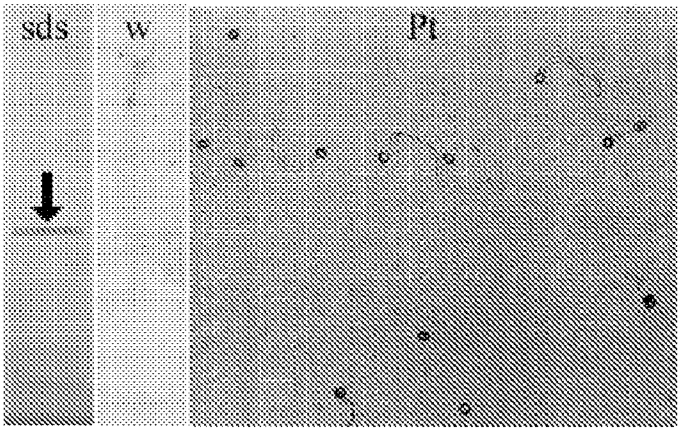
(c) LWW + ProtK
Fig. 2 A

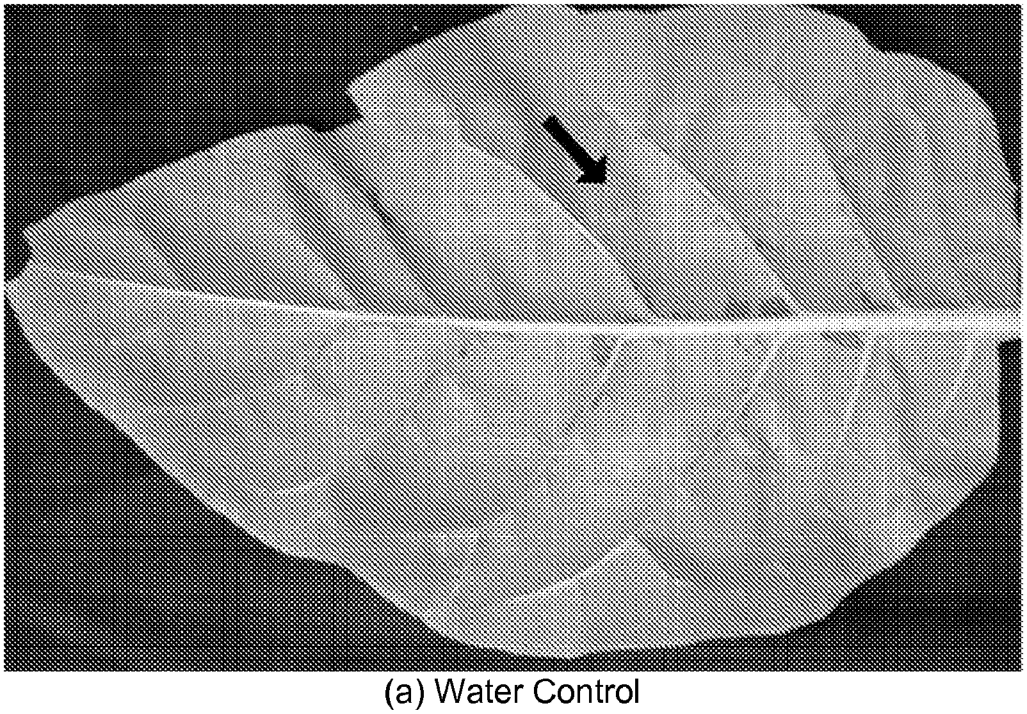
(a) Water Control
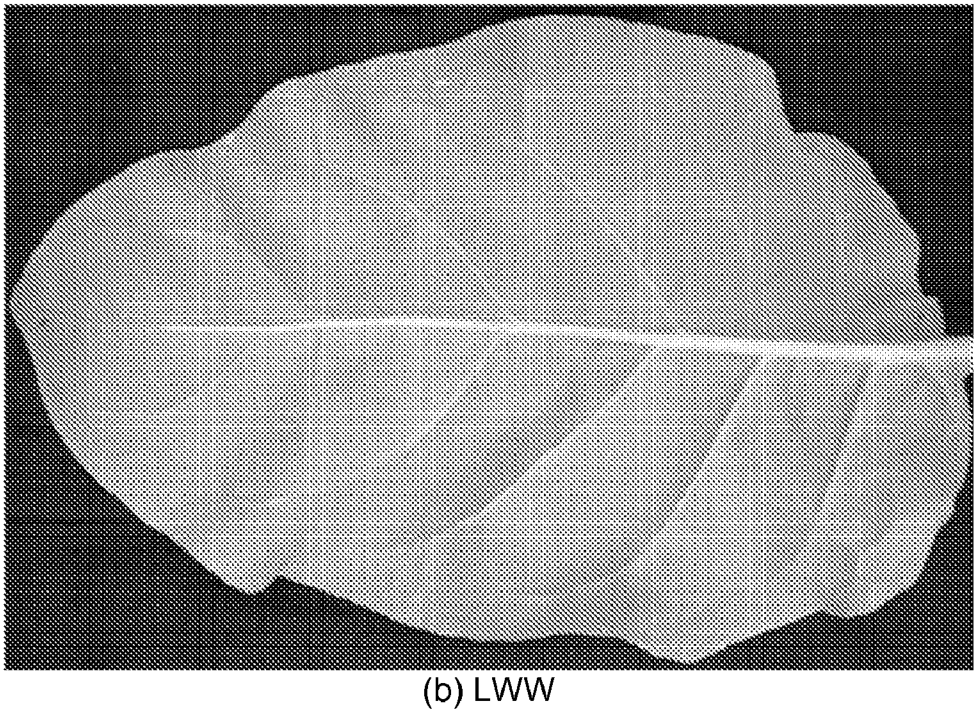
(b) LWW
Fig. 2 B

```
                                                 M   A   S
AACACAATTTCTTACAGCAATAACTATCACATATAACAATAACTGCC ATG GCT TCA   56

 A   K   I   F   L   I   F   L   L   A   A   L   I   A   T
GCA AAA ATT TTC TTG ATT TTC CTT TTG GCT GCA TTA ATC GCA ACC  101
                    aa-N1-
 P   A   A   F   A   I   L   V   P   T   L   V   S   T   H
CCC GCT GCA TTT GCC ATA CTT GTT CCA ACA CTT GTT TCA ACA CAT  146
                                -aa-N1
 I   S   G   L   V   F   C   S   V   N   G   N   L   D   V
ATA AGT GGG CTT GTA TTT TGC AGC GTT AAC GGC AAT TTA GAT GTC  191
                                            aa-T1-
 I   N   G   L   S   P   Q   V   F   P   N   A   S   V   Q
ATC AAC GGA CTC AGT CCC CAA GTT TTT CCT AAT GCA TCA GTG CAA  236
 -aa-T1 aa-T2-                                 -aa-T2
 L   R   C   G   A   T   N   V   I   S   S   T   I   T   N
TTG CGG TGT GGA GCA ACA AAT GTG ATA TCA AGT ACA ATA ACA AAT  281

 G   S   G   A   F   S   L   A   V   N   T   F   P   L   L
GGA TCG GGA GCA TTT TCC TTG GCG GTG AAT ACT TTC CCA CTG CTA  326
            aa-T3-
 N   C   N   L   V   V   A   T   P   L   S   T   C   N   A
AAC TGC AAT TTA GTG GTT GCA ACT CCA CTA TCA ACA TGT AAC GCG  371
                -aa-T3
 T   L   Q   S   V   G   R   L   A   S   S   L   R   L   V
ACC TTA CAA TCG GTT GGG CGT TTG GCG TCA TCC TTG AGA CTT GTA  416
                                        aa-P1-
 N   I   T   L   G   S   G   T   G   L   I   R   V   G   L
AAT ATC ACT CTT GGC AGT GGC ACC GGT CTT ATT AGA GTC GGT TTA  461
         -aa-P1     aa-T4-          -aa-T4
 A   P   T   G   F   I   L   N   L   N   I   N   *
GCT CCT ACT GGT TTT ATA CTT AAT CTT AAC ATC AAT TAA TATTGAAC 508
GAGCTAGCCTGCTGGTTCTTAATTAGTACTACTACTATGCATCAGCTAGTTAACTTTCTT 568
GGCCAGCTGCTTACTGCAAGAATAAGGACTGTTGTTTCCACTAGTGAATAAAGTGCAAAT 628
CATATTTGCAAGTCTAAAAAAAAAAAAAAAAAAAAAAA                       666
```

Fig. 4

```
-1157 cccattccac tatgaacttc ccggaattca attctgacta tgcgtacaag tcataatgaa
-1097 gctgcacata gccttcatat cgctaaacga cgtgctaggt ctcaaaacga cctgtcgggg
-1037 tcgttacatt agaggtgatt aacttcgtgt atacttgtgc aagtgttcta taacaatttc
 -977 aggccaacct agtaagagta gaaatagtga atggcacata acaaacgatc accacgaaat
 -917 gtacatgata taactcacac aaggtaggca cgctactaga caattaccaa taacaacaat
 -857 gcctaggaca tcacaagata tgaaaaatca atccttacta tcacggttga gttgtaacgt
 -797 gtaagaatat ttcacacttt ttagggcact aagatcactc caccaacatt tcaagagaat
 -737 cactggcact gccaaaaagc cctctacact gtagtgaatt tttgttagtt atctaaagtt
 -677 aattattcac ttagtattct ttacattagg ttcccccctt ctaggtcctg cacgtaacta
 -617 gattgaatgg attggtccac tctattatta cagagtaatt attaaatttt tatttgacta
 -557 ggcaacacta attgcactat caacaaagta ttagttctag ccttctgggt acttcatacc
 -497 tatgcaaatg ataattttat ttaaaacaat agatgtacat ggatataaat acctatgaaa
 -437 attaaataaa atataactaa gaaaaaaaat ttaaagttca ctcctaagat atcgggttat
 -377 tacatgacca aacacaattt gtttatcaaa tactttcaaa agaatttgtc aaacgtaaat
 -317 tatttttctc caaagtgact tatgaattac tatgttgata aaatactttt caaagtaact
 -257 aatgtttaga agtcaaggat gggcttcttt tgattattga agtttgtagc aattgtatgt
 -197 agttatagtc agggtgacca ccagcatctc atatagcaat acacaagtgg gttagcgtat
 -137 ttgaaatttc aattagttca ttcaaatata cacgtaatag cattataagc cactttcaca
  -77 acagatagat taggggtttt aaaatttcaa ccaatgatat ttactataaa ttgatcatgc
  -17 acaaacctta attgagcaac acaatttctt acagcaataa ctatcacata taacaataac
            M  A   S  A  K   I  F  L  I   F  L  L   A  A  L (SEQ ID NO:18)
  +44 tgccatggct tcagcaaaaa ttttcttgat ttcctttttg gctgcatta
```

FIG. 8

METHOD UTILIZING THE TOBACCO PHYLLOPLANIN PROMOTER FOR EXPRESSION OF NUCLEIC ACIDS AS GENE PRODUCTS DIRECTED TO AERIAL SURFACES OF PLANTS

CROSS REFERENCE TO RELATED APPLICATIONS

This patent claims priority to U.S. Provisional Application Ser. No. 60/777,383, filed Feb. 28, 2006, herein incorporated by reference.

FIELD OF THE INVENTION

The present invention relates to a method and system for delivering protein and protein products to plant surfaces and, in particular, a method and system for delivering protein products to plant surfaces using specific promoter sequences.

BACKGROUND OF THE INVENTION

In plants, surface protection is an innate defensive strategy in which microbes are directly inhibited at their first point of host contact, usually at the boundary between the host and the external environment. While studies of chemical-based leaf surface protection in plants have focused on secreted secondary metabolites, e.g., glandular trichome exudates, animal studies have focused on secreted surface proteins deployed at host/pathogen interfaces such as skin or intestinal epithelia, as reported by Gallo and Huttner (1998); and Schroder (1999), both herein incorporated by reference.

Fungi and fungi-like, e.g., oomycete, pathogens are the major causes of plant disease, resulting in annual crop losses of ~20% worldwide, forcing extensive control by synthetic fungicides. Many of these organisms reproduce via airborne spores and transiently exploit the plant leaf surface, or phylloplane, as a starting point for host ingress. Spores of the oomycete pathogen *Peronospora tabacina*, the causal agent of blue mold disease on several *Nicotiana* species, germinate on the leaf surface by forming a germination tube, and then penetrate the plant epidermal layer with an "infection peg." For successful phylloplane germination to occur, spores must tolerate pre-formed biochemicals present on the leaf surface.

While some surface biochemicals are presumed to leach passively from the leaf interior, e.g., sugars, others are selectively biosynthesized by specialized epidermal cells for delivery to the phylloplane. Trichomes are simple or glanded epidermal appendages that occur on most plants. Glandular secreting trichomes are found on ~30% of vascular plants, and they produce surface-accumulated exudates that usually contain hydrophobic isoprenoids and phenylpropanoids, the latter including flavonoids, phenolics, tannins, quinones, etc. In Solanaceae plants, amphipathic sugar esters are also commonly found in glandular trichome exudates. Such compounds have been associated with insect resistance in many plants, and pest resistance is often correlated with glandular trichome density. Two well-studied cases of glandular trichome-based insect resistance are found in the plant family Solanaceae. Sugar esters produced by tall glandular trichomes (TGSTs) of primitive tomato and potato species, and the diterpenoid cembratriene-ol produced by tobacco TGSTs, have been shown to inhibit aphid infestation. Antimicrobial activities of trichome exudate compounds, particularly monoterpenoids and sesquiterpenoids, have also been reported, but are less-studied than insect resistance.

In plants, the aerial surface is referred to as the phylloplane. In a region of the phylloplane referred to as the phyllosphere, a habitat is epitomized by specialized interactions between host plants and microorganisms, both pathogenic and epiphitic. Other regions of the phyllosphere may include epidermal cell wall spaces, the spaces inside guard cell and hydathode stoma, and leaf inner air space.

In *Nicotiana tabacum*, phylloplane structures include guard cells, hydathodes, simple trichomes, glandular secreting trichomes with their exudates, other epidermal cells, and the cuticle. Glandular secreting trichomes, guard cells and cuticular components have been studied, and their roles in pathogen and insect interactions have been reviewed. Recent attention has been given to molecular aspects of simple trichome differentiation and development in *Arabidopsis* and cotton, and the apparent roles of simple trichomes in microbial disease resistance, as affected by physical impedance to disease transmitting insects and water shedding, are documented in the literature. In contrast, the structure and function(s) of hydathodes are poorly understood, even though guttation, secretion of primarily, but not exclusively, water at the leaf surface, has been observed in many species.

The best studied tissue for secretion of antimicrobial components to the epidermal surface is the glandular secreting trichome. Perhaps 30% of vascular plants possess exudating glandular trichomes. Depending on the species, varying amounts of various biochemicals, often lipophylic, often terpenes, are produced, secreted, and accumulated by this specialized tissue type. A common form of glanded trichome is the peltate type, having an aggregate of one or more specialized gland tip cells attached by a stalk to aerial plant surfaces. Secreting trichome glands of this type produce and secrete exudate into the space outside gland cells, enclosed by a cuticle surrounding the gland. Exudate chemicals may escape this containment via pores referred to as striae in the cuticle, and run down the stalk onto the epidermal surface where they are thought to primarily serve the plant as anti-insect or anti-microbe defense agents, as described in Wagner, G. J., Wang, E., Shepherd, R. W. (2004) "New approaches for studying and exploiting an old protuberance, the plant trichome." *Annals of Botany* 93: 3-11, herein incorporated by reference. Insects walking on the surface may disrupt the cuticle and become immobilized by viscous exudates, or poisoned. Airborne spores or moisture-facilitated motile spores or bacteria reaching the plant surface may contact trichome exudate that has been distributed on the surface. Thus, trichome exudation has been viewed as a first line of defense against pests and pathogens. Glandular trichome exudates may contain a wide variety of chemicals, many of which are terpenoids. Other exudate constituents are flavanoids, phenolics, and sugar esters. The amount of accumulated trichome exudate can vary widely with species and growth conditions. Hydathodes, like glandular secreting trichomes, are secreting structures that are positioned to deliver biochemicals to the leaf surface.

It has long been recognized that when the soil is moist and the air is cool and humid, leaves of many plants, particularly young leaves, will bear small liquid droplets at the leaf margin or distributed on the entire surface. This moisture is often mistaken for dew, but is generally thought to be guttated water, with some solute, presumed to be primarily inorganic salts. Hydathodes may be specialized single cells at leaf margins or stalked multicellular structures as found throughout the surface, often along veins and at vein junctures, on tobacco leaves. The most important feature of hydathodes that sets them apart from simple and glandular trichomes is their intimate connection to the xylem. The hydathode "gland" consists of very loose parenchyma cells located at the end of one more small veins. This tissue is called the epithem. In most hydathodes the epithem is surrounded by a layer of tight fitting cells called the sheath, which consists of cells that have cutinized, endodermis like, adjacent walls. It has been said that there is always at least one stoma, called a water pore, in hydathode sheaths. These pores are often larger than guard cell stoma and it is generally thought that in hydathodes of most plants, the pore cannot be closed, as described in Mauseth, J. D. (1988) *Plant Anatomy*, The Benjamin/Cummings Publishing Co., Inc., Chapter 9, pp. 141-166, herein incorporated by reference. A possible function of hydathodes in young leaves with immature and non-functioning stomata and poorly developed vascular tissues is to facilitate acquisition of an ample supply of mineral nutrients for rapid growth by removing xylem transported nutrients into the hydathode sheath cells while allowing the water to exit through the pore. Transfer cells with plasmalemma and cell wall ingrowths that are characteristic of cells engaged in massive solute membrane transport are found in hydathode sheath cells.

Much of what is known about the structure and function of hydathodes comes from the older literature and, while very important, it is largely descriptive and does not elucidate details about cell-level mechanisms of hydathode function. For example, the diversity of solutes that may be present in guttation water is not known, or how they are delivered to it, or if guttation is restricted to young leaves. Several recent studies using sensitive, cell-selective detection methods, such as promoter-GUS localization, show distinct chitinase gene expression in hydathodes, as well as several other tissues. Similarly, intense production of auxin in developing leaf hydathodes was correlated with vascular differentiation using a fusion of a highly active synthetic auxin response element with GUS. Also, using GUS fusions with *arabidopsis* purine transporter genes, evidence was obtained that these transporters may be involved in retrieval from vascular fluid of nucleobases and derivatives in hydathodes, presumably to prevent their loss by guttation. Using energy-dispersive X-ray analysis, it was recently shown that in tobacco plants exposed to very high Cd, hydathodes, called short trichomes, and also glandular trichomes, secrete Cd to the extent that Cd-containing crystals form on the external surfaces of these structures. Guttation fluid of barley, *Hordeum vulgare*, seedlings was recently shown to contain pathogenesis-related proteins, which, it was suggested, may inhibit motile bacteria entering the plant through open hydathode water pores. As in many grasses, leaf tips of barley seedlings have hydathodes with large water pores.

SUMMARY OF THE INVENTION

The present invention relates to a system for delivering protein and protein products to a plant surface using a phylloplanin promoter, in conjunction with a nucleic acid gene sequence, whose product one wishes to be excreted by a plant. The phylloplanin promoter provides for surface-localized proteins to be generated when the promoter is fused with the desired gene.

The present invention, in one form, relates to a method for generating excreted gene products in a plant. The method includes generating a nucleic acid fusion construct comprising a phylloplanin promoter and a selected non-phylloplanin nucleic acid sequence whose transcription product is to be expressed and delivered to an aerial surface of a plant. Plant cells are transfected using the nucleic acid fusion construct and the plant cells are allowed to express the non-phylloplanin nucleic acid sequence transcription product which is excreted from the plant cells. In one form, the phylloplanin promoter is from tobacco and has the nucleic acid sequence of SEQ ID NO:1, as shown in FIG. 8.

The plant species to which the present method can be adapted, includes but in not limited to *Medicago* sp., *Trifolium* sp., *Ulmus* sp., *Pyrus malus, Prunus armeniaca, Cynara acolymus, Asparagus officinale, Hordeum* sp., *Galium* sp., *Beta vulgaris, Prunus serotina, Vigna sinensis, Nyssa sylvatica, Quercus* sp., *Artocarpus altilis, Brassica* sp., *Andropogon scoparius, Fagopyrum sagittatum, Manihot esculenta, Apium graveolens, Agropyron desertorum, Cornus florida, Phaseolus* sp., *Triticum* sp., *Oenothera caespitosa, Carya* sp., *Lactuca* sp., *Impatiens* sp., *Helianthus* sp., *Ledum decumbens, Astragalus pattersoni, Setaria italica, Vaccinium mytrillus, Avena sativa, Petroselinum crispum, Pastinaca sativa, Pisum* sp., *Prunus* sp., *Pyrus communis, Musa paradisiaca, Astragalus preussii, Raphanus sativus, Secalse cereale, Sassafras albidum, Atriplex confertifolia, Tillandsia usneoides, Spinacia oleracea, Liquidambar styraciflua, Linaria triphylla, Liriodendron tulipfera, Vicia* sp., *Citrullus vulgaris, Melilotus* sp., *Salix* sp., *Rhus copallina, Nicotiana* sp., *Vitis* sp., *Datura* sp., *Medicago* sp., *Lycopersicon* sp., *Solanum* sp., *Capsicum* sp., *Cucumis* sp., *Fragaria* sp., *Petunia* sp., *Geranium* sp., *Coleus* sp., *Stevia* sp., *Oryza* sp., *Nepeta* sp., *Zea mays, Glycine max*, and *Arabidopsis thaliana*.

The present invention, in another form thereof, relates to an isolated nucleic acid sequence comprising a nucleic acid fusion construct comprising a phylloplanin promoter and a selected non-phylloplanin nucleic acid sequence. The selected non-phylloplanin nucleic acid sequence may encode an amino acid sequence selected from the group consisting of a pharmaceutical, cosmeceutical, and a nutriceutical agent.

BRIEF DESCRIPTION OF THE FIGURES

FIG. 2A comprises panels (a)-(c), depicting *P. tabacina* spore germination assay (Pt), Coomassie blue-stained SDS-PAGE gel blot (sds), and protein gel blot with a 1:10,000 dilution of phylloplanin antiserum (w), wherein panel (a) is a gel water plus spores; panel (b) is a gel TI 1068 LWW (diluted to 100 ng/μL total protein) plus spores; and panel (c) is a gel TI 1068 LWW (100 ng/μL total protein) digested with proteinase K (ProtK) plus spores, where the arrow marks residual, soluble proteinase K; and FIG. 2B comprises panels (a) and (b) for *P. tabacina* leaf infection assay of cv Petite Havana, where panel (a) is a photograph of water plus spores ($10^4$ spores/mL), a sporulating lesion is indicated with the arrow; and panel (b) is a photograph of TI 1068 LWW (diluted to 50 ng/μL) plus spores ($10^4$ spores/mL).

FIG. 4 is the nucleotide (SEQ ID NO:19) and predicted amino acid sequence (SEQ ID NO:20) of T-Phylloplanin cDNA with nucleotide numbered on the right and start and stop codons underlined, and the signal sequence in bold-faced segments corresponding to peptides aa-N1, aa-T1, aa-T2, aa-T3, aa-T4, and aa-P1 marked by lines above the amino acid sequence and labeled.

FIG. 6A is *E. coli* expressed MBP-PhyllP (M-P; 160 ng/μL total protein) treated with Factor-Xa, an arrow indicates released T-PhyllP; FIG. 6*b* is *E. coli* expressed MBP-T-PhyllP (160 ng/μL total protein) treated with Factor-Xa and Proteinase-K (ProtK), where the volume used was equivalent to that of FIG. 6A; FIG. 6*c* is *E. Coli* expressed MBP (M; 200 ng/μL total protein) treated with Factor-Xa; and FIG. 6D is *E. Coli* expressed MBP (200 ng/μL total protein) treated with Factor-Xa and ProtK, where the volume used was equivalent to that used in the experiment of FIG. 6C.

FIG. 8 depicts the promoter sequence of the gene Phylloplanin (SEQ ID NO:1), having a putative TATA box (−33 to −30) and a putative CAAT box (−47 to −43) bold-faced, where the phylloplanin transcription start site (+1) is indicated bold-faced and underlined, the phylloplanin start codon (+48) is underlined, and a portion of the phylloplanin amino acid sequence (SEQ ID NO:18) is indicated.

DETAILED DESCRIPTION

Figure 1:
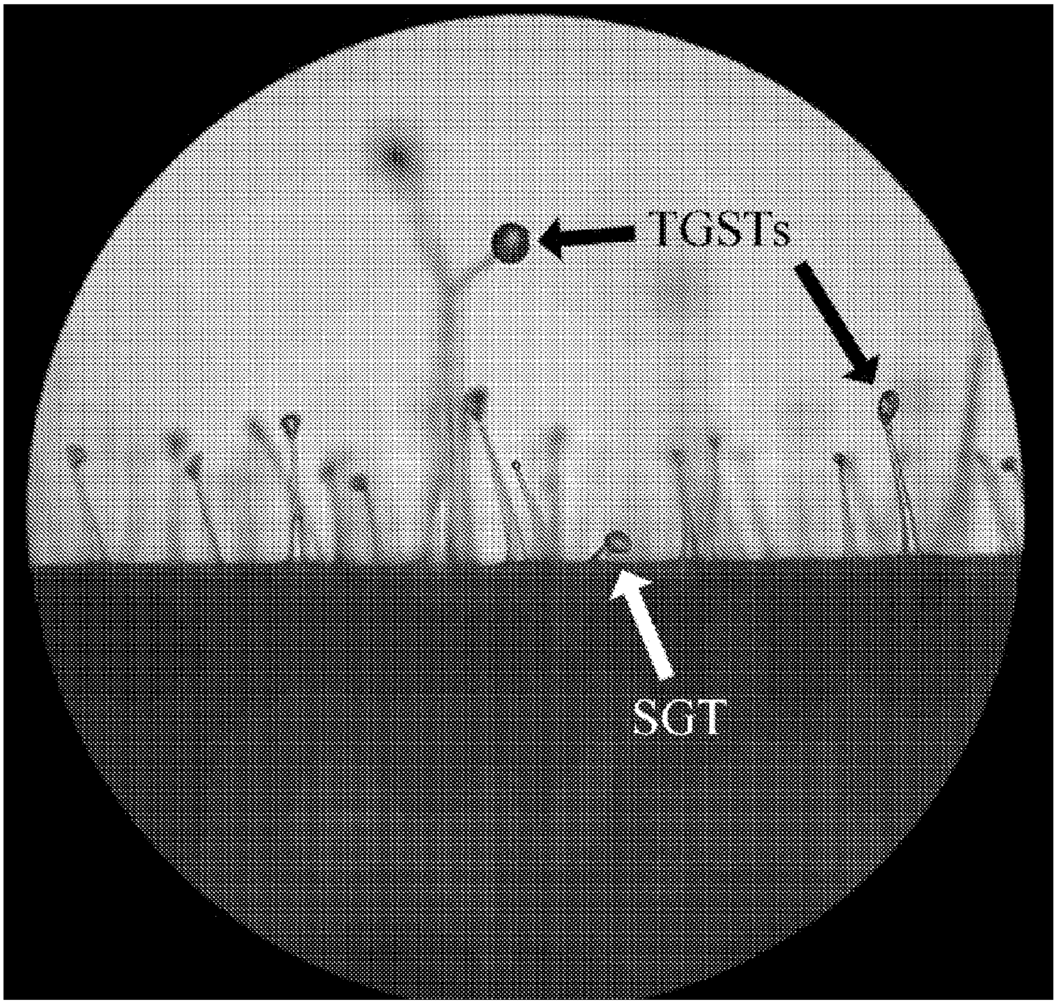
FIG. 1A is a 40× magnification of TI 1068 phylloplane with tall glandular secreting trichomes (TGSTs) and short glandular trichome (SGTs) identified.
FIG. 1B is a Coomassie blue-stained SDS-PAGE of TI 1068-derived samples, in which phylloplanins I-IV are identified, and loaded volumes of LWW (lane d) and sterile-grown plant LWW (lane e) represent 25 $cm^2$ leaf surface area, and Mwt (lane a) denotes protein standards.
FIG. 1C is a silver-stained SDS-PAGE of LWWs from field-grown TI 1068 (lane b; 10 $cm^2$), *G. max* (lane c; 30 $cm^2$), and *H. annuus* (lane d; 6 $cm^2$), where Mwt (lane a) denotes protein standards.
Figure 1:
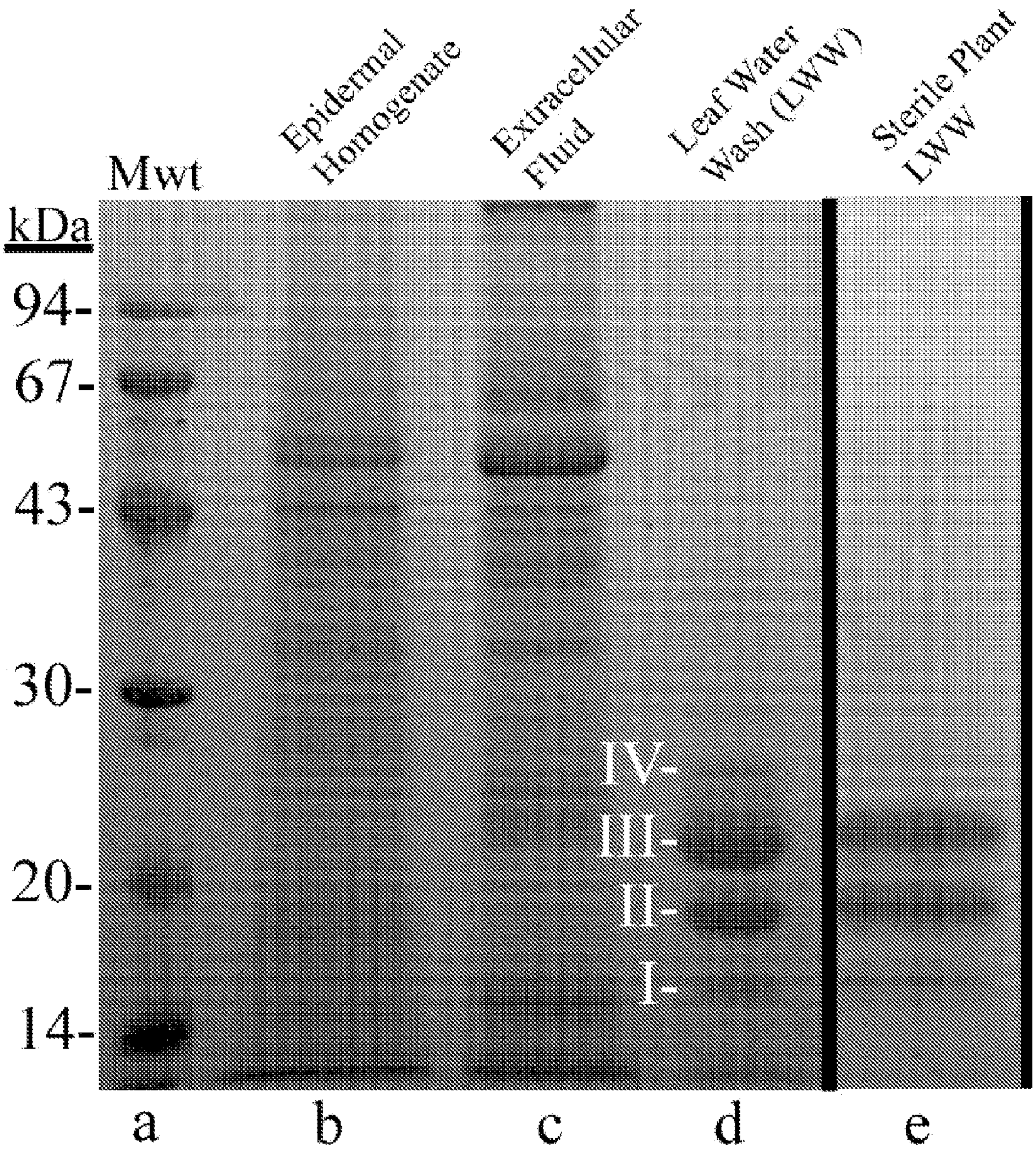
Figure 1:
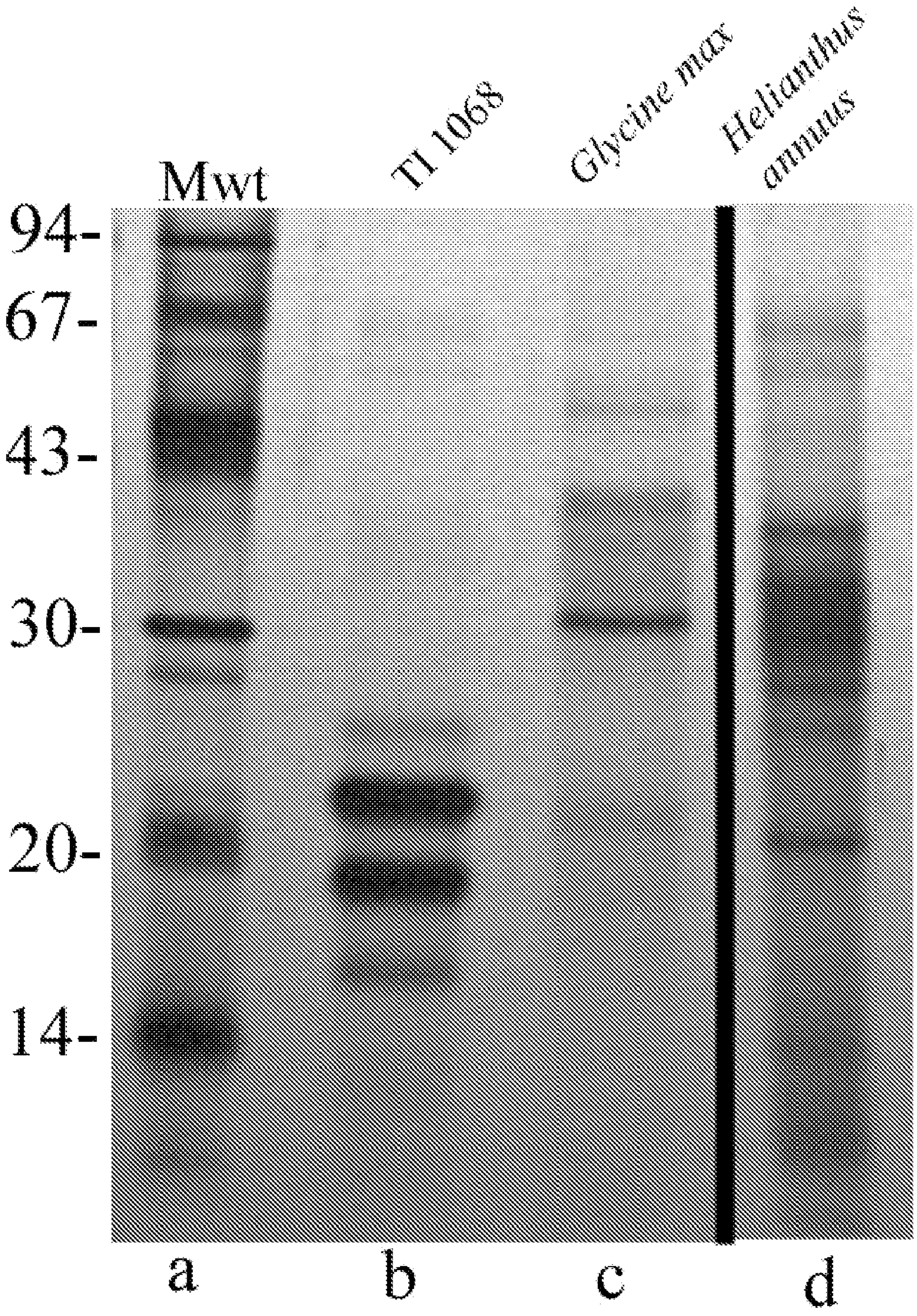

The generation of excreted gene products using a phylloplanin promoter to express and deliver the desired product to a plant's aerial surface was developed from studying gene promoter sequences from plants, such as tobacco, where the expression of genes in plants is controlled by a number of regulatory components, including nucleic acid and protein elements, and where the initiation is controlled by a region commonly referred to as a "promoter," which lies upstream (5') of the protein in the coating region. The phylloplanin gene promoter has previously been isolated and sequenced from the surface of plant leaves, and was further found to essentially control the production of proteins known as phylloplanin in plants, as described in U.S. patent application Ser. No. 11/304,528, herein incorporated by reference.

The promoter sequence of the gene phylloplanin is provided in FIG. 8. The phylloplanin promoter drives the secretion of gene products to leaf aerial surfaces. As used throughout this disclosure, the surface-localized proteins referred to as tobacco phylloplanins are generated in nature from the novelty-phylloplanin promoter from *N. tabacum.*

The T-phylloplanin promoter can be inserted into various plant species to drive desired protein product to plant aerial surfaces, which includes, but is not limited to *Medicago* sp., *Trifolium* sp., *Ulmus* sp., *Pyrus malus, Prunus armeniaca, Cynara acolymus, Asparagus officinale, Hordeum* sp., *Galium* sp., *Beta vulgaris, Prunus serotina, Vigna sinensis, Nyssa sylvatica, Quercus* sp., *Artocarpus altilis, Brassica* sp., *Andropogon scoparius, Fagopyrum sagittatum, Manihot esculenta, Apium graveolens, Agropyron desertorum, Cornus florida, Phaseolus* sp., *Triticum* sp., *Oenothera caespitosa, Carya* sp., *Lactuca* sp., *Impatiens* sp., *Helianthus* sp., *Ledum decumbens, Astragalus pattersoni, Setaria italica, Vaccinium mytrillus, Avena sativa, Petroselinum crispum, Pastinaca sativa, Pisum* sp., *Prunus* sp., *Pyrus communis, Musa paradisiaca, Astragalus preussii, Raphanus sativus, Secalse cereale, Sassafras albidum, Atriplex confertifolia, Tillandsia usneoides, Spinacia oleracea, Liquidambar styraciflua, Linaria triphylla, Liriodendron tulipfera, Vicia* sp., *Citrullus vulgaris, Melilotus* sp., *Salix* sp., *Rhus copallina, Nicotiana* sp., *Vitis* sp., *Datura* sp., *Medicago* sp., *Lycopersicon* sp., *Solanum* sp., *Capsicum* sp., *Cucumis* sp., *Fragaria* sp., *Petunia* sp., *Geranium* sp., *Coleus* sp., *Stevia* sp., *Oryza* sp., *Nepeta* sp., *Zea mays, Glycine max*, and *Arabidopsis thaliana*.

As discussed in further detail below, evidence that the phylloplanin can be used to drive plant aerial secretion of desired gene products is provided by experiments using the T-phylloplanin promoter, fused with reporter genes beta-glucuronidase and green fluorescent protein, in which biosynthesis was directed only in apical-tip cell clusters of short, procumbent glandular trichomes. Accordingly, the reporter gene studies provide evidence for a method and system for directing protein excretion to a plant's aerial surfaces, thus allowing one to use the T-phylloplanin to drive the excretion of desired protein products to plant aerial surfaces.

The following non-limiting experiments are included to provide additional understanding and evidence which supports the present invention, but in no way limits its scope.

Referring now to FIGS. 1A-1C, SDS-PAGE analyses of leaf water wash (LWW) from greenhouse-grown TI 1068 leaves indicated the presence of four bands with molecular masses of 16 (I), 19 (II), 21 (III), and 25 (IV) kDa (FIG. 1B, lane d), collectively termed T-phylloplanins. T-Phylloplanins in LWW were relatively pure and abundant, compared to proteins present in leaf epidermal cells (FIG. 1B, lane b) or leaf extracellular fluid (FIG. 1B, lane c), providing evidence of selective deployment on the phylloplane. Sterile-grown TI 1068 LWW contained T-phylloplanins (FIG. 1B, lane e), indicating these proteins were not formed by leaf surface microbes and were not induced by pathogen attack. From measurement of the protein concentration in LWW (BCA assay), an estimate was made that the phylloplane of greenhouse-grown TI 1068 leaves contains 100-200 ng protein/square-cm leaf surface. Field-grown TI 1068 LWW also contained T-phylloplanins, indicating that leaf surface proteins are present under natural conditions (FIG. 1C, lane b), and T-phylloplanins were renewed after washing (data not shown). *N. tabacum* cultivars TI 112 and TI 1406 that lack TGSTs or secretion, respectively, produce substantial T-phylloplanins (data not shown), so diterpene/sugar ester producing TGSTs are not the site of T-phylloplanin biosynthesis. Field-grown soybean and sunflower LWWs contained varying amounts of phylloplanins (FIG. 1C, lanes c-d), as did greenhouse-grown corn, tomato, soybean, and potato (data not shown), but these proteins were not further characterized. LWW of frozen TI 1068 leaves that were cold-brushed to completely remove TGSTs and SGTs contained a similar amount of T-phylloplanins per unit surface area to that found in LWW of undisturbed leaves, indicating that T-phylloplanins are not restricted to SGTs but are rather generally dispersed on the leaf surface. T-Phylloplanins Inhibit *Peronospora tabacina* Spore Germination and Leaf Infection

*P. tabacina* is an oomycete pathogen that reproduces via airborne spores, and initial host contact and spore deposition commences at the phylloplane. LWW from greenhouse-grown TI 1068 plants inhibited *P. tabacina* spore germination (FIG. 2A, panel b; $LD_{50}$~15-20 ng/μL [50 spores/μL]), as did LWW from sterile-grown plants (data not shown). Protein digestion by immobilized Proteinase K relieved inhibition of spore germination (FIG. 2A, panel c), indicating that proteins were necessary for inhibition. Spore germination was not affected by water incubated with immobilized Proteinase K (data not shown). Also, once spore germination was initiated, addition of LWW (100 ng/μL total protein) immediately arrested germination tube growth and development (data not shown). Using GC, the levels of residual exudate diterpenes found in LWW (data not shown) were <1/10 of the $LD_{50}$ reported to inhibit *P. tabacina* germination, and nicotine was unable to be detected in LWW (data not shown).

Intact *N. tabacum* Petite Havana SR1 plants, considered susceptible to *P. tabacina*, were infected by applying spores (50 spores/μL in 4 μL water) to the leaf surface. After 5 days, sporulating lesions developed at sites of application (FIG. 2B, panel a). T-phylloplanins in TI 1068 LWW, when mixed with spores at total protein concentrations of 50 ng/μL or higher, inhibited leaf infection by *P. tabacina* (FIG. 2B, panel b). At 25 ng/μL total protein, 75% inhibition was observed, and no inhibition occurred with titrations below 12.5 ng/μL total protein (data not shown). Similar results were observed in three independent experiments and in identical experiments using the susceptible cultivar KY 14 (data not shown).

Figure 3:
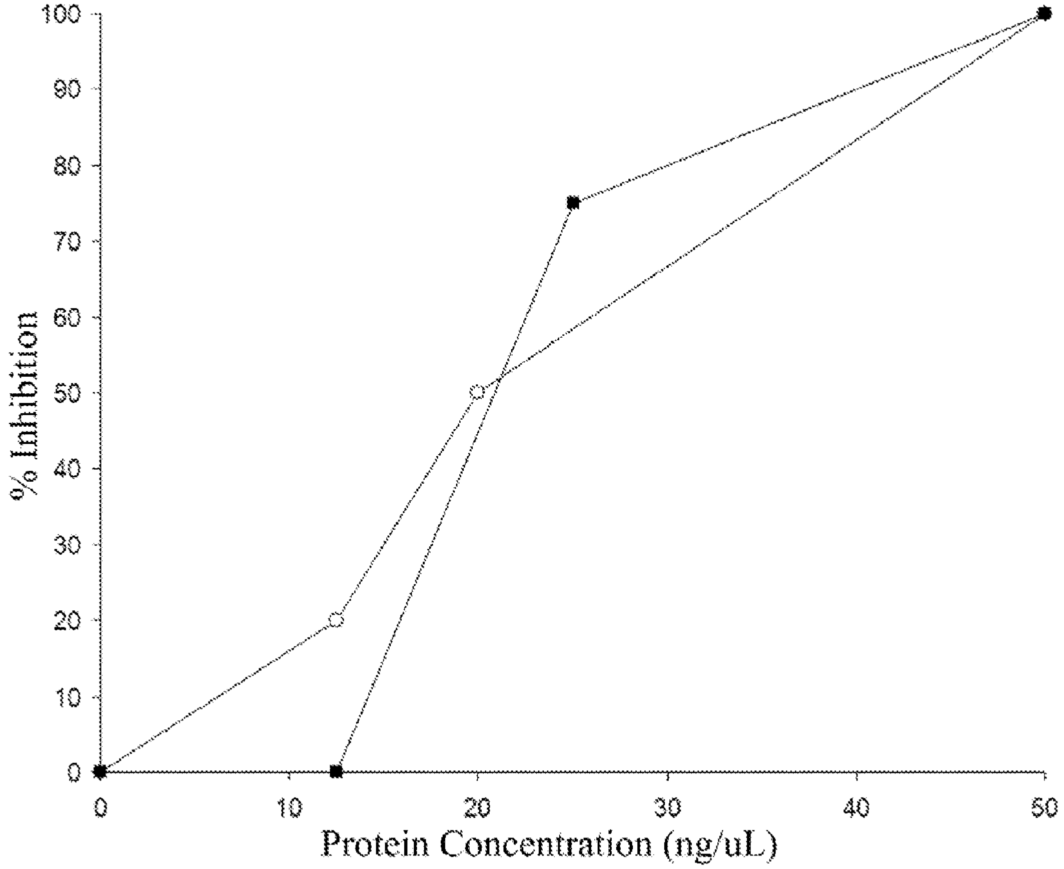
FIG. 3 is a plot depicting inhibition of *P. tabacina* spore germination (open circles) and leaf infection (closed squares) by T-phylloplanins in LWW, where, for both assays, results of a single experiment represent three separate experiments conducted.

Referring now to FIG. 3, the graph shows the inhibitory effect of T-phylloplanins in LWW on *P. tabacina* spore germination and leaf infection. LWWs of Petite Havana and KY 14 contain less phylloplanins I-IV than TI 1068, and unlike TI 1068 they produce low trichome exudate (data not shown). Based on these results, it is believed that other surface chemicals (e.g., surface lipids or TGST trichome exudate components) may influence or accentuate phylloplanin activity, dispersion, or longevity, by acting as adducts or as solubilizing agents. Thus a combination of T-phylloplanins and high TGST exudates may provide maximal inhibition of spore germination. It is difficult to estimate the role of a single component such as T-phylloplanins in blue mold susceptibility or resistance, outside the experimental conditions used here, but we propose that T-phylloplanins are a key component.

Isolation of the Novel T-Phylloplanin Gene

*N. tabacum* T-phylloplanins I, II, III, and IV share an identical N-terminal amino acid sequence (Table).

TABLE

| Method | Peak (min) | T-phyllo-planin | Amino Acid Sequence | SEQ ID NOs. | Name |
|---|---|---|---|---|---|
| N-terminus | N/A | I | ILVPTLVST | SEQ ID NO:21 | |
| | N/A | II | ILVPTLVSTHISGLVF-CSV | SEQ ID NO:22 | aa-N1 |
| | N/A | III | ILVPTLVSTHISGLVF-CSV | SEQ ID NO:23 | aa-N1 |
| | N/A | IV | ILVPTLVSTHISGLVF-CSV (major) | SEQ ID NO:24 | aa-N1 |
| Trypsin | 36.2 | I | ASVQLR | SEQ ID NO:25 | aa-T1 |
| | 59.8 | I | ILNLNI (major) | SEQ ID NO:26 | aa-T4 |
| | | | CGATNVISSTIT (minor) | SEQ ID NO:27 | aa-T2 |
| | 56.7 | III | LVVATPLSTCxATLx-SVG | SEQ ID NO:28 | aa-T3 |
| | 58.7 | III | ILNLNI (major) | SEQ ID NO:29 | aa-T4 |
| | | | CGATxVxSSTIT (minor) | SEQ ID NO:30 | aa-T2 |
| Pepsin | 35 | I, II, III, IV | IRVGLAPTG | SEQ ID NO:31 | aa-P1 |

Amino acid sequences recovered from T-phylloplanin N-terminal analyses, trypsin digestion, and pepsin digestion.
N/A, not applicable.

Internal amino acid sequences were elucidated from peptides generated by trypsin digestion of T-Phylloplanins II and IV, and pepsin digestion of total LWW (Table). Degenerate, deoxyinosine-containing primers were synthesized and used in RT-PCR with cDNA generated from *N. tabacum* total leaf RNA as a template, and a 332 base pair fragment was amplified. RLM-RACE was used to recover a full-length, novel *N. tabacum* T-Phylloplanin cDNA sequence (SEQ ID NO:9) (FIG. 4; Accession AY705384) of 666 base pair in length, encoding a hydrophobic, basic (50% hydrophobicity, estimated pl 9.3, Vector NTI) 15.4 kDa protein containing 150 amino acids. Based on the N-terminus recovered from the mature T-phylloplanin (lle-24) the first 23 amino acids comprise a signal sequence that targets the protein to the secretory pathway. The molecular mass of the mature protein is estimated to be ~13 kDa. A protein of this mass was not recovered from the leaf surface but, instead, four apparent bands of higher molecular masses were recovered. While differences in amino acid composition may account for differences in migration, the molecular masses of native T-phylloplanins I-IV could be increased due to the occurrence of covalent adducts with cuticular lipids, or trichome exudate diterpenes or sugar esters. These covalent adducts would be retained in SDS-PAGE, and they could serve to increase phylloplanin solubility in TGST exudate (diterpenes and sugar esters) and aid in phylloplanin dispersion on the leaf surface. Amphipathic sugar esters (~24% of TI 1068 weight) are known to solubilize largely hydrophobic diterpenes (~73%) of TGST exudate. Highly hydrophobic, basic, saposin-like proteins of animals (see below) also display anomalous migration in SDS-PAGE (Curstedt et al., 1987), which provides evidence that T-phylloplanins may behave similarly.

BLAST searches conducted in accordance with Altschul et al. (1990) with the T-Phylloplanin gene sequence against the non-redundant and EST GenBank databases yielded several significant hits from *Nicotiana* sequences, including an AFLP fragment from *N. tabacum* (GenBank accession number AJ538724) and several EST sequences from *N. tabacum* and *N. sylvestris*. BLAST searches also indicated that homologous genes of unknown functions exist in many other plants. A ClustalW alignment (DNASTAR software, Madison, Wis.) between T-Phylloplanin and selected sequences giving significant tBLASTn scores from various other plant species (FIG. 5A) indicated that regions of amino acid identity exist and possibly represent conserved motifs.

Figure 5:
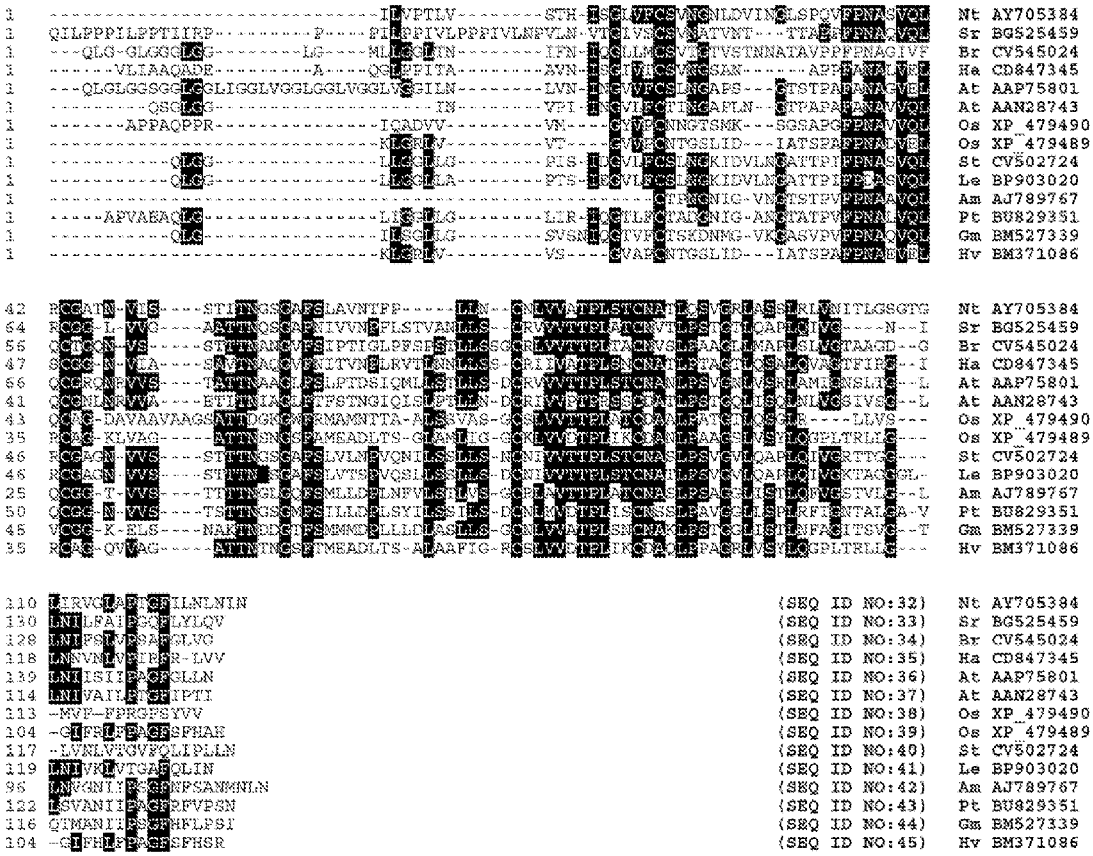
FIG. 5A is the amino acid sequence of T-Phylloplanin aligned against sequences giving significant BLAST similarity scores, using the CLUSTALW algorithm of DNASTAR Lasergene software, where amino acids conserved between any six sequences are indicated in reverse contrast.
FIG. 5B is an unrooted phylogenetic tree showing evolutionary relationships between the sequences in FIG. 5A with bootstrap values >50% given on the respective branches, where the first two letters of the acronyms indicate the species (Br, *Brassica rapa*; Ha, *Helianthus annuus*; At, *Arabidopsis thaliana*; Nt, *Nicotiana tabacum*; Gm, *Glycine max*; Pt, *Populus tremuloides*; Le, *Lycopersicon esculentum*; Os, *Oryza sativa*; St, *Stevia tuberosum*; Am, *Antirrhinum majus*; Sr, *Stevia rebaudiana*), where the GenBank accession numbers of the sequences follow the species identifiers, and tissue localizations of ESTs and cDNAs are indicated beneath the acronyms.
Figure 5:
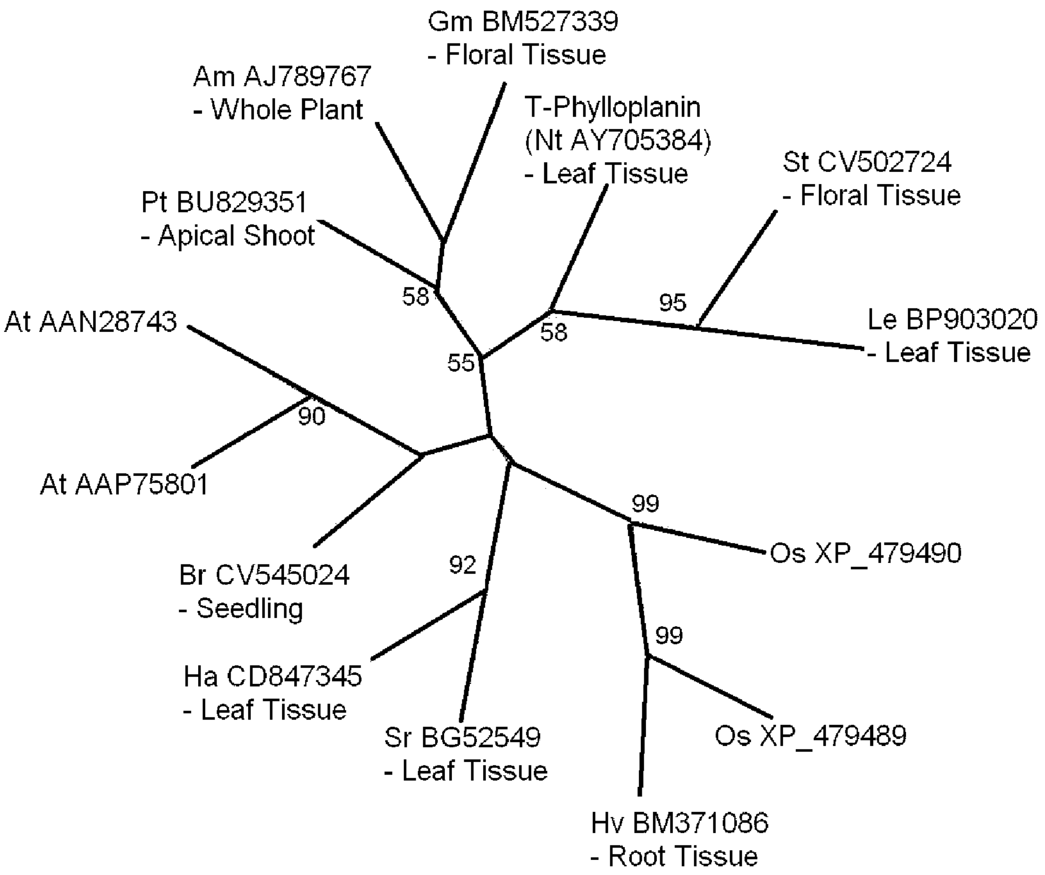

An unrooted phylogenetic tree is provided in FIG. 5B to show evolutionary relationships between these sequences and to indicate the tissue localizations of ESTs. The tree indicates that T-phylloplanin groups with similar sequences from other solanaceous plants that also bear glandular secreting trichomes, and it is intriguing that the *S. tuberosum* gene is expressed in floral tissue which may bear trichomes. Similar sequences from the monocots *O. sativa* and *H. vulgare* also form a distinct group in the phylogenetic tree, with the gene from *H. vulgare* being expressed in root tissue. The genomic structure of gene T-Phylloplanin was elucidated from *N. tabacum* genomic DNA using a Genomewalker kit. The gene contains two exons (1:175 bp; 2:278 bp) that are separated by a 508 bp intron (data not shown).

*E. coli*-expressed T-Phylloplanin Inhibits *Peronospora tabacina*

Figure 6:
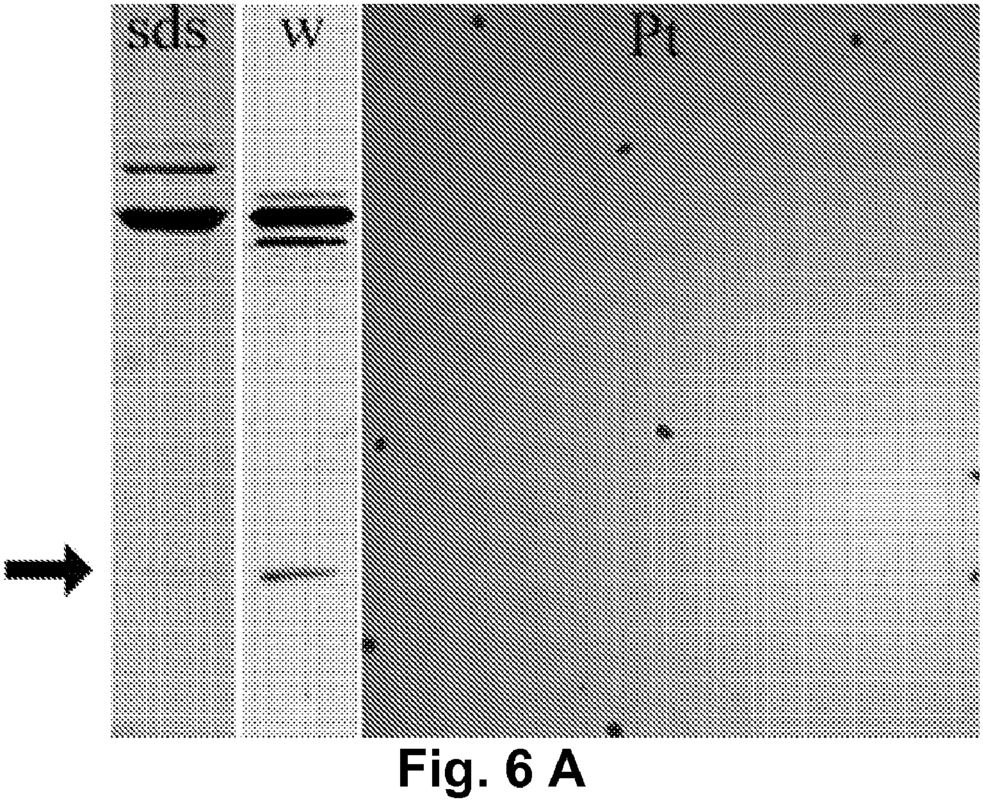
FIGS. 6A-6D depict Coomassie blue-stained SDS-PAGE western blots with 1:10,000 T-phylloplanin antiserum (w), and *P. tabacina* spore germination assays (Pt), where
Figure 6:
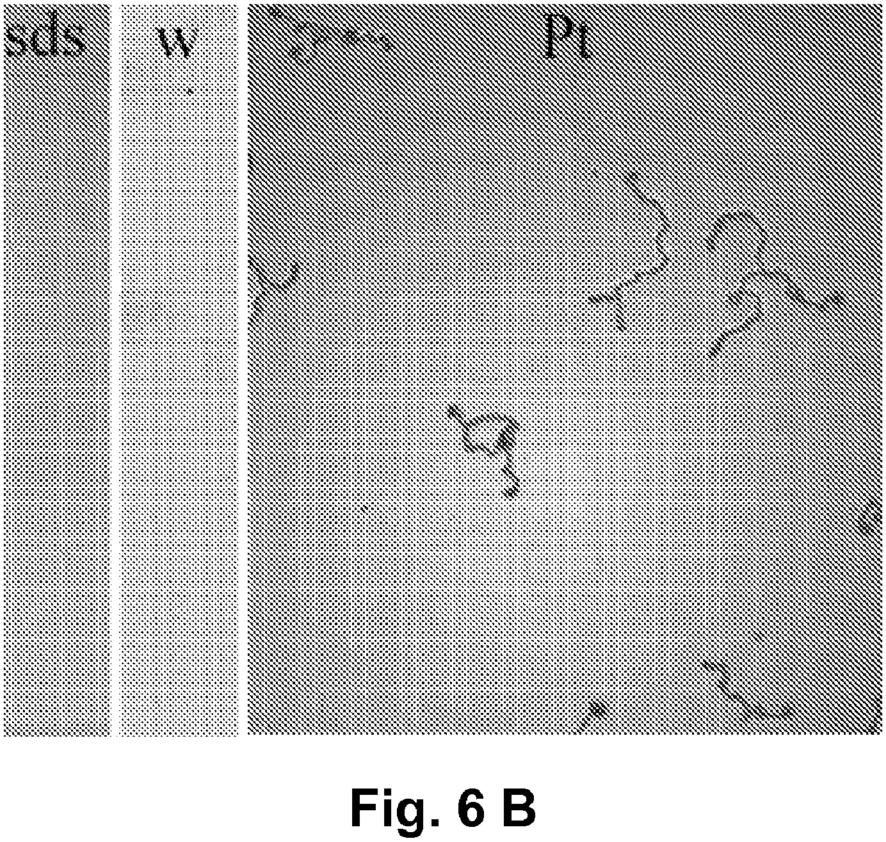
Figure 6:
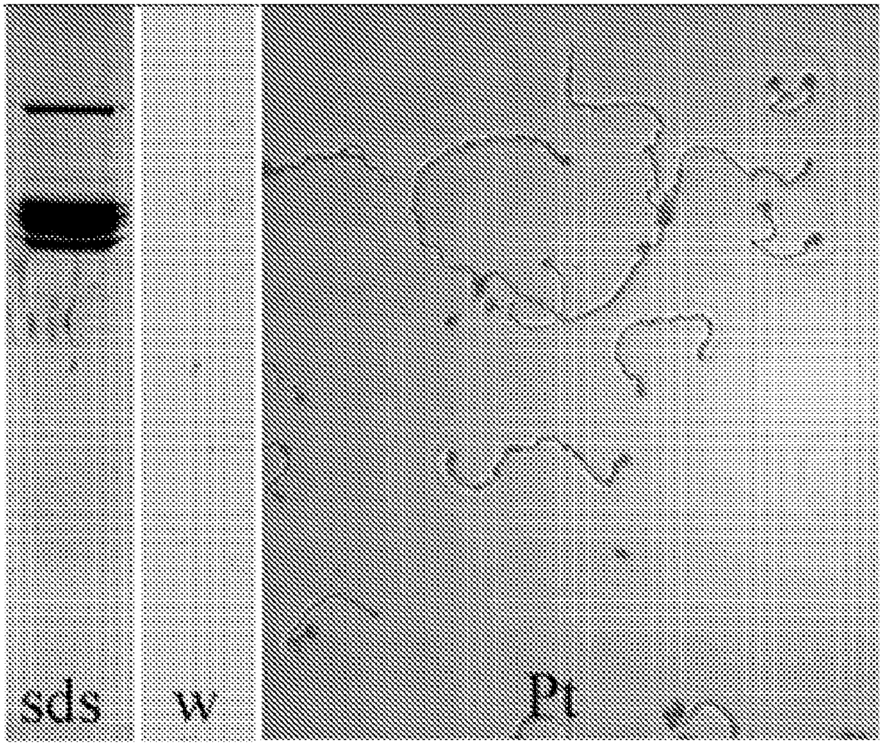
Figure 6:
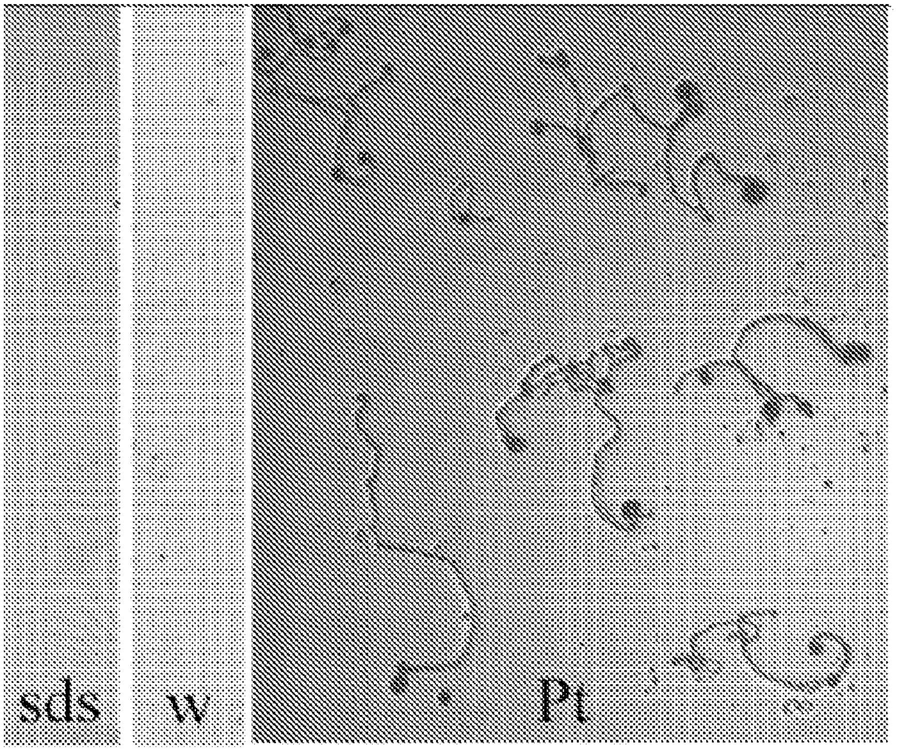

A 10.3 kDa portion of the T-Phylloplanin gene (T-PhyllP) was expressed in *E. coli* as a fusion protein with MBP. Soluble fusion protein (MBP-T-PhyllP) was purified on an amylose column, cut with the protease Factor Xa to release T-PhyllP, and desalted on a 3 kDa centrifugal filter. Both MBP-T-PhyllP and T-PhyllP reacted with the phylloplanin-specific antibody, as shown in FIGS. 6A-6D. The sample containing T-PhyllP inhibited *P. tabacina* spore germination at total protein concentrations greater than 160 ng/μL (FIG. 6A). Protease digestion relieved T-PhyllP inhibition of spore germination (FIG. 6B). A control sample containing MBP alone, produced by an empty pMal-c2x vector and treated exactly as the T-PhyllP sample, had no effect on spore germination (FIG. 6C), nor did protease-treated MBP (FIG. 6D), at total protein concentrations <500 ng/μL. No inhibition of spore germination was observed with MBP-T-PhyllP fusion protein not treated with Factor Xa (data not shown). Based on the data, the released T-PhyllP is responsible for the observed inhibition, and since it is evident (FIG. 6A, SDS gel) that released-T-PhyllP is a minor component of the sample (<10% total protein), the inhibitory concentration of T-PhyllP is considered <<160 ng/μL. T-PhyllP was lost when purification from MBP and Factor Xa was attempted (data not shown).

In leaf infection assays performed with KY 14 plants, T-PhyllP did not totally inhibit infection, but it greatly reduced necrotic leaf damage. MBP and uncut MBP-T-PhyllP fusion samples allowed successful infections (data not shown). The lack of total inhibition with T-PhyllP may be due to insufficient protein concentration, the absence of another interacting protein, or alternatively, speculated-adducts with lipids or trichome exudate components are essential for a native-protein like response.

Figure 7A:
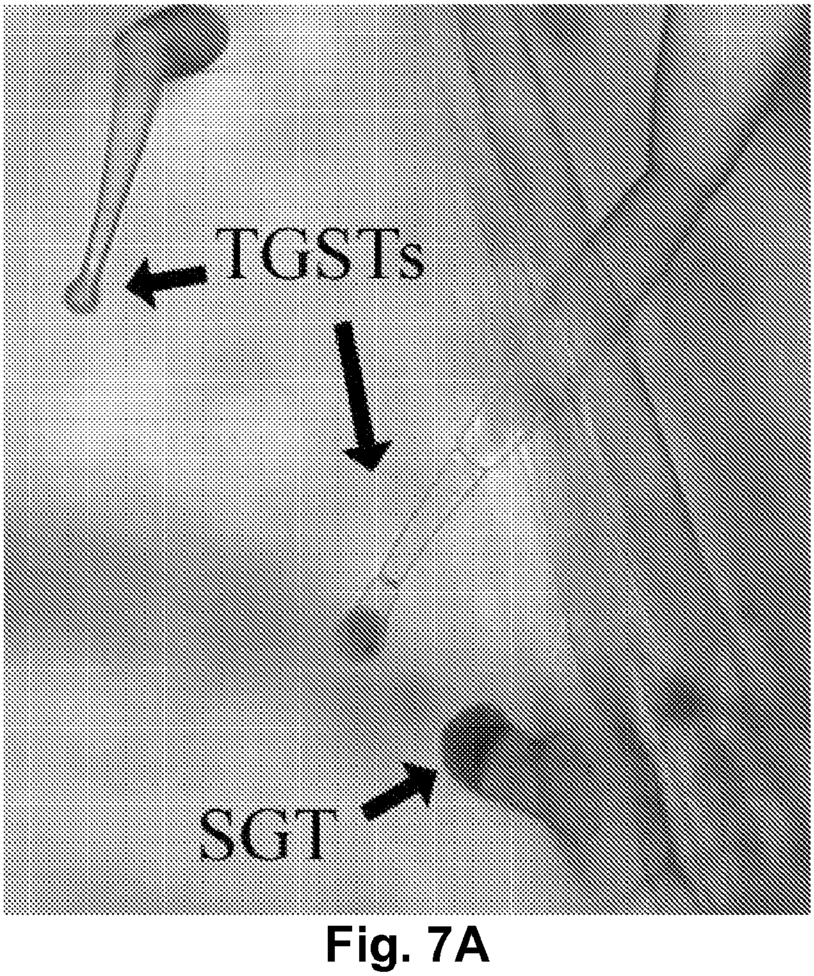
FIG. 7A is a magnification of a 5-bromo-4-chloro-3-indolyl-β-glucuronic acid-stained plantlet leaf from TI 1068 with GUS under the control of the T-phylloplanin promoter, where TGSTs are indicated.
Figure 7B:
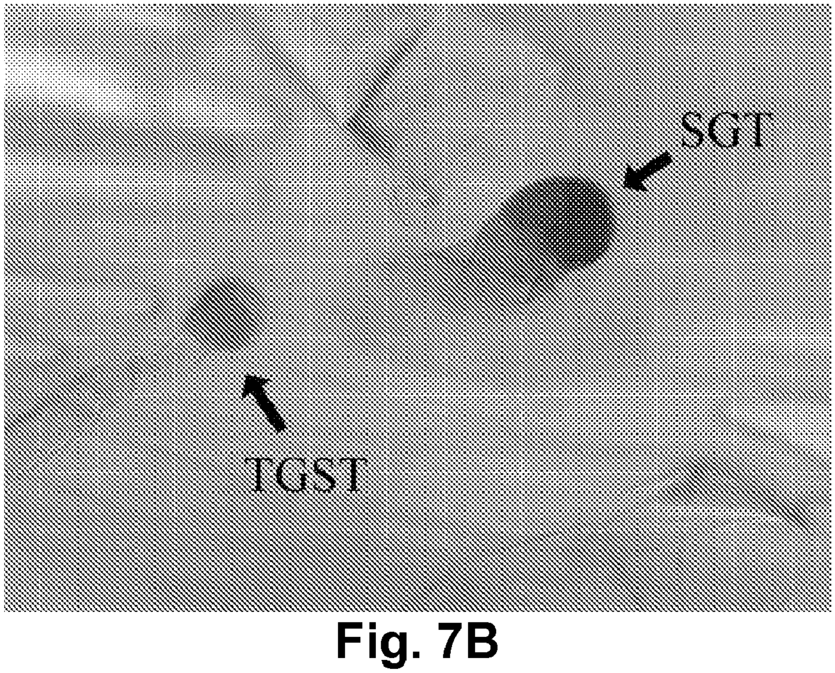
FIG. 7B is X-gluc stained SGT on TI 1068 plantlet expressing GUS under control of T-phylloplanin promoter, where surface structures are indicated.

The T-Phylloplanin Promoter Region Directs Expression in Small Glandular Trichomes 1.8 kb of genomic DNA sequence upstream from the T-Phylloplanin transcription start site was elucidated. A 1.1 kb region of this DNA, as well as the 5'UTR and the T-Phylloplanin signal sequence, was fused in-frame with the reporter genes β-glucuronidase (GUS) and Green Fluorescent Protein (GFP) and introduced into TI 1068 plants using *Agrobacterium* mediated transformation. GUS and GFP were expressed only in SGTs (FIGS. 7A-7C), indicating activity of a SGT-specific promoter. There was no evidence that GUS or GFP exit the SGTs. This is not surprising in that these reporter proteins are water soluble. TI 1068 SGTs are uniformly distributed over the leaf surface and protrude over surrounding epidermal cells (FIG. 7A). The data provides evidence that T-phylloplanins are biosynthesized locally in SGTs and are secreted to the leaf surface where, because of their hydrophobicity and basicity, T-phylloplanins dissolve in TGST exudate and are dispersed widely on the leaf surface during exudate flow. Certain animal saposin proteins are also highly hydrophobic and basic, are secreted by epithelial cells, and operate as components of innate immunity at the pulmonary air/water interface.

Figure 7C:
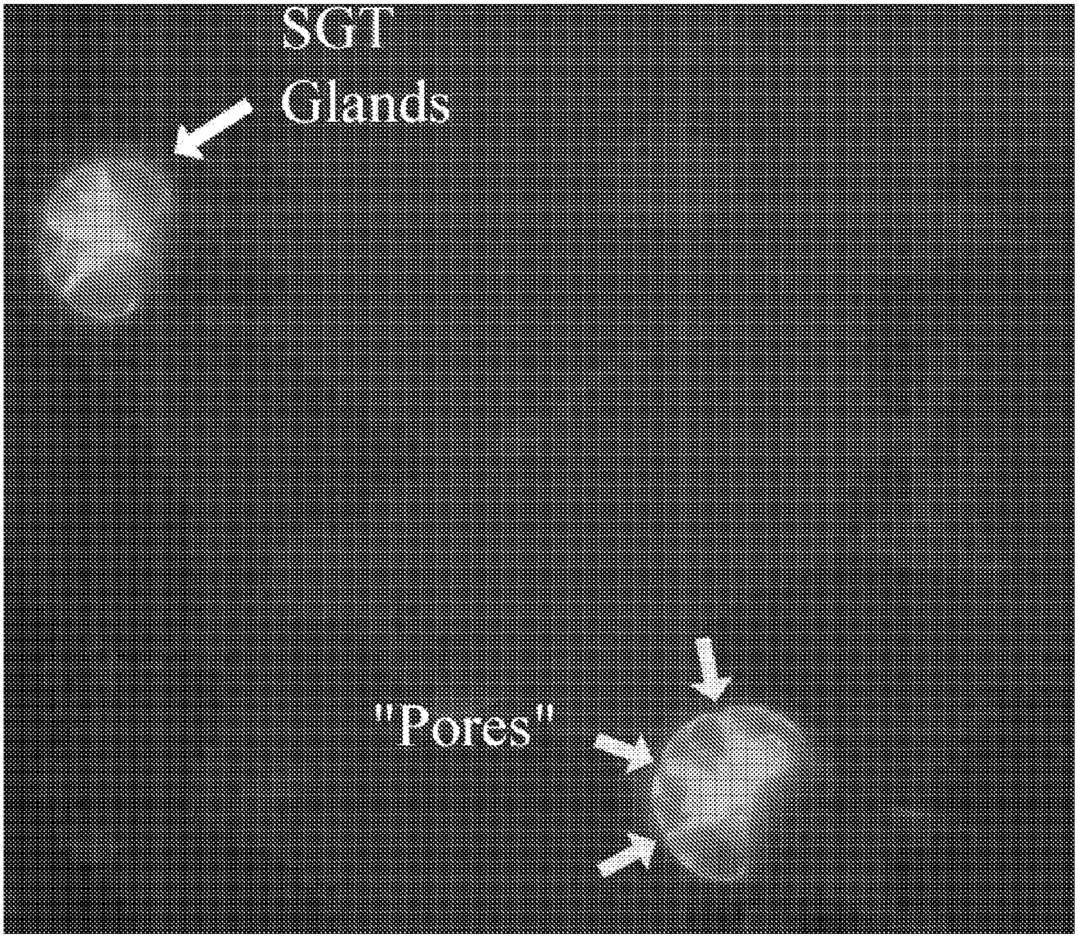
FIG. 7C is fluorescent magnification/detection of TI 1068 plantlet with GFP under control of T-phylloplanin promoter, where GFP was present only in SGT gland cells, and arrows indicate constrictions between gland cells that we speculate may be pores to release protein to the leaf surface.

Ultrastructural studies defined the subcellular structures of *N. tabacum* cv. Xanthi SGTs and TGSTs. Glands of procumbent SGTs were observed to have about four cells separated by large, specifically-oriented intracellular spaces that contained substantial $OsO_4$ stained material. The nature of the accumulated substance was not defined, but it is believed that this substance is T-phylloplanins, since the pattern of intracellular space disposition observed is strikingly similar to that which we have observed here using the T-phylloplanin-promoter-GFP construct (FIG. 7C). All tobaccos examined but one, smooth leaf *N. glauca*, produce phylloplanins. The data provides evidence that T-phylloplanins are produced in SGT gland cells, and that they are secreted to gland extracellular spaces, and then transferred outside the glands through constrictions at termini of intracellular spaces forming “secretory pores” (arrows, FIG. 7C) of unknown structure.

The majority of plant pathogens are fungi. When airborne spores land on a leaf surface, germination is the initial step leading to host colonization. It is hypothesized that by rapidly inhibiting spore germination at the leaf surface, preformed plant proteins may suppress pathogen infection before induced defenses become functional, in a manner analogous to secreted surface proteins of animals. This hypothesis is supported by the observations that surface-accumulated *N. tabacum* T-phylloplanins and *E. coli*-expressed T-PhyllP inhibit *P. tabacina* spore germination in vitro and limit leaf infection in situ. The hypothesis is also supported by the observation that the T-phylloplanin promoter directs reporter gene expression specifically in SGTs, and T-phylloplanins are retained on leaves from which trichomes were completely removed by brushing of frozen tissue.

The aforementioned observations provide evidence that T-phylloplanins are secreted to and broadly dispersed on the leaf surface. Three observations link the gene T-Phylloplanin to T-phylloplanin proteins collected from the leaf surface. First, all amino acid sequences recovered from leaf surface T-phylloplanins I-IV are present in the predicted protein sequence from T-Phylloplanin, representing 54% of the mature protein open reading frame. Secondly, there is a functional link between the gene and the proteins by replicating LWW blue mold inhibition with *E. coli*-expressed T-PhyllP. The T-phylloplanin promoter is a third, critical link between the gene and surface disposed T-phylloplanins, and implicates SGTs as the sites of T-phylloplanin biosynthesis and delivery to the surface.

Secreted phylloplanins, e.g., T-phylloplanins, represent a novel leaf surface defense system in tobaccos, and perhaps generally in the plant kingdom, wherein protein biosynthesis in a specific trichome type allows deposition and dispersion of phylloplanins on leaf aerial surfaces to deter pathogen establishment. Further, from the collected data, the T-phylloplanin promoter can be used to direct protein products to plant aerial surfaces.

Methods

Biological material and growth conditions. Greenhouse plants (*Nicotiana tabacum* L. tobacco introduction, (TI) 1068, TI 1112, TI 1406; cultivars KY 14 and Petite Havana SR1 [hereafter referred to by TI number or cultivar name]) were germinated and grown in soil under natural light at 22-24° C. with weekly fertilization (20-20-20, N-P-K). Plants were transplanted into 15-cm pots and treated with the insecticide Marathon (Olympic Horticultural Products, Mainland, Pa.) at 3-4 wk post-emergence. Field plants (TI 1068, *Glycine max, Helianthus annus*) were grown at a farm near Lexington, Ky. during the 2002 growing season.

To grow sterile TI 1068 plants, seeds were immersed in 10% (v/v) sodium hypochlorite for 10 min, rinsed briefly in 70% (v/v) ethanol, washed 4 times in sterile water, and germinated on Murashige-Skoog (MS) medium (Murashige and Skoog, 1962) containing B5 vitamins (100 mg/L myo-inositol, 10 mg/L thiamine-HCl, and 1 mg/L each pyridoxine-HCl and nicotinic acid) in a 22° C. growth chamber under fluorescent illumination (light/dark 16/8 h daily). Individual plants were transferred to PlantCons (ICN Biomedicals, Aurora, Ohio) containing MS agar at 3 weeks post-emergence.

*E. coli* strain ER2508 (New England Biolabs, Beverly, Mass.) was stored and propagated as described by the supplier. Spores of *Peronospora tabacina* (isolate KY-79) were harvested from sporulating lesions on KY 14 plants as described (Reuveni et al., 1986).

Phylloplanin collection and SDS-PAGE. Water-soluble phylloplane components were collected in LWWs from mature, fully-expanded leaves of all greenhouse-grown and field-grown plants by washing freshly-detached leaves in 200 mL nanopure water for 15 s (NANOpure water system D4751, Barnstead/Thermolyne, Dubuque, Iowa). Cut petioles or cut leaf surfaces were not exposed to wash solutions.

LWWs were filtered (No. 1 filter paper, WHATMAN, Clifton, N.J.), lyophylized to dryness, resuspended in 3 mL sterile water, and centrifuged at 12,000×g for 5 min at 21° C. The supernatants were filtered (13 mm/0.45-μm syringe filter, Corning Glass Works, Corning, N.Y.) to exclude bacteria and fungi.

Proteins were separated by SDS/12%/glycine-PAGE (Laemmli, 1970) or SDS/15%/tricine-PAGE (Judd, 1994) using a MINI PROTEAN II electrophoresis system (BIO-RAD Hercules, Calif.), according to the manufacturer's instructions, and visualized with Coomassie blue or silver staining.

Protein concentration was estimated using the bicinchoninic acid assay (Pierce Chemical, Rockford, Ill.) with BSA as a standard. Leaf surface areas were estimated by tracing leaves onto uniform-weight paper and weighing the cutouts.

Collection of epidermal peels and extracellular fluid (EF). Epidermal peels were prepared from greenhouse-grown TI 1068 plants as described (Kandra et al., 1990), pulverized with liquid $N_2$, and proteins were analyzed by SDS-PAGE. EF was collected using a vacuum infiltration method (Terry and Bonner, 1980) and analyzed by SDS-PAGE.

GC analysis. Trichome exudate was collected from greenhouse-grown TI 1068 by immersing unwashed leaves for 15 s in 200 mL acetonitrile. The wash solutions were filtered (No. 1 filter paper, Whatman), dried, and trichome exudate was resuspended in 5 mL acetonitrile and quantified by GC (flame ionization detection) as trimethylsilyl derivatives prepared in dimethylformamide, as previously described (Wang et al., 2001). To determine the amounts of trichome exudate biochemicals occurring in LWW, volumes equivalent to 200 $cm^2$ leaf surface areas were transferred to glass GC vials and dried in a vacuum oven (37° C.) overnight. Trichome exudate biochemicals were extracted at 21° C. with methylene chloride, dried, solubilized, derivatized, and analyzed by GC. The amount of residual trichome exudate biochemicals in LWW was assessed relative to total trichome exudate on an equivalent surface area basis.

T-Phylloplanin aa sequencing. Proteins in greenhouse-grown TI 1068 LWW were separated by SDS-PAGE, transferred to polyvinyldifluoride (IMMOBILON—PSQ, Millipore, Bedford, Mass.) using a MINI PROTEAN II electroblot apparatus (BIO-RAD), and visualized with Coomassie blue. T-Phylloplanin bands were subjected to N-terminal sequencing using automated Edman degradation (Matsudaira, 1987) at the University of Kentucky Macromolecular Structure Analysis Facility (Lexington, Ky.). To recover internal amino acid sequence information, LWW from greenhouse-grown TI 1068 was separated by SDS-PAGE, stained with Coomassie blue, and 21 kDa and 19 kDa bands were excised and digested with trypsin. Total proteins in TI 1068 LWW were also digested with pepsin. Resulting tryptic or peptic peptides were separated by reversed-phase HPLC (Aquapore RP-300 7 μm particle size, octyl reversed-phase column [Applied Biosystems, San Jose, Calif.]), manually collected based on absorbance at 214 nm, and samples were reduced in volume under vacuum to ~50 μL. Amino acid sequence analyses of tryptic peptides were performed as above. For peptic peptides, similar analyses were performed at The Protein Facility of Iowa State University (Ames, Iowa).

Degenerate RT-PCR, RLM-RACE, and Elucidation of Genomic Structure. Total RNA was extracted from TI 1068 leaf tissue (100 mg fresh weight [FW]) with an RNEASY kit (Qiagen, Chatsworth, Calif.), and cDNA was synthesized from 5 μg total RNA using an Omniscript RT kit (Qiagen). PCR was performed using PCR master mix (Promega, Madison, Wis.) containing 3 μL cDNA template and 4 μM of each primer in a 50 μL volume. Successful amplification of a PCR product occurred with the primers 5'-ACWTTNGTNTCNACWCATATYTCNGGNCTNGTYTTTTG-3' (SEQ ID NO:2) and 5'-AARAANCCIGTNGGNGCNARNCCNACYCTAAT-3' (SEQ ID NO:3) where N=Inosine, W=A or T, Y=C or T, and R=A or G. Amplification was for 46 cycles using the following thermal profile: 95° C. for 45 s, 50° C. for 45 s, 72° C. for 1 min, followed by a final 4 min extension at 72° C. The PCR product was size-fractionated by electrophoresis in a 1% (w/v) agarose gel, extracted using a QIAEX II kit (QIAGEN), cloned into a pGem-T vector (Promega), and sequenced.

For RNA ligase mediated rapid amplification of cDNA ends (RLM-RACE), total RNA was extracted from TI 1068 leaf tissue, as above. A GENERACER kit (Invitrogen, Grand Island, N.Y.) containing SUPERSCRIPT III was used to generate cDNAs, according to the manufacturer's instructions. Successful amplification of a 3'RACE product occurred with the GENERACER 3'Primer and the gene-specific primer 5'-CTCAGTCCCCAAGTTTTTCCTAATGCATCAG-3' (SEQ ID NO:4). Successful amplification of a 5'RACE product occurred with the GeneRacer 5'Primer and the gene-specific primer 5'-GGCCAAGAAAGTTAACTAGCTGATGCATA-3' (SEQ ID NO:5). PCR cycling parameters were according to the GENERACER protocol.

T-Phylloplanin genomic structure was elucidated using a GENOMEWALKER kit (Clontech, Palo Alto, Calif.), according to the manufacturer's protocol, using genomic DNA isolated from TI 1068 leaf tissue (100 mg FW) with a DNEASY plant kit (QIAGEN). Primary PCR reactions were performed with a sense outer adaptor primer AP1, provided in the kit, and the antisense T-Phylloplanin-specific primer (5'-

TGGAACMGTATGGCAAATGCAGCGGGG-3') (SEQ ID NO:6). Primary PCR cycling parameters were 7 cycles of 25 s at 94° C. and 3 min at 72° C., followed by 32 cycles of 25 s at 94° C. and 3 min at 67° C., with a final extension of 7 min at 67° C. Products of primary PCR were diluted 1:25 and 1 μL was used in nested PCR reactions with a sense inner adaptor primer (AP2), provided in the kit, and a nested antisense T-Phylloplanin-specific primer (5'-GGGGGTTGCGATTAATGCAGCCAAAAGGAAAA-3') (SEQ ID NO:7). Nested PCR cycling parameters were 5 cycles of 25 s at 94° C. and 3 min at 72° C., followed by 20 cycles of 25 s at 94° C. and 3 min at 67° C., with a final extension of 7 min at 67° C. Amplified PCR products were amplified, size fractionated by gel electrophoresis, gel-extracted, cloned into pGem-T, and sequenced.

Expression vector construction and fusion protein purification. To overexpress the T-Phylloplanin gene in *E. coli*, a 10.3 kDa portion of the coding sequence (His33-Gly142, termed PhyllP) and the full-length mature protein coding sequence (Ile24-Asn150) were amplified incorporating XbaI and PstI restriction sites (PhyllP-sense: 5'-AGCT TCTAGACATATTTCGGGGCTGGTTTT (SEQ ID NO:8); PhyllP-antisense: 5'-AGCT CTGCAGTTAGCCGGTGGGGGCGAGGCC-3' (SEQ ID NO:9); Full-sense: 5'-AGCT TCTAGAATACTTGTTCCAACACT-3' (SEQ ID NO:10); Full-antisense: 5'-AGCT CTGCAGTTAATTGATGTTAAGA-3' (SEQ ID NO:11); restriction sites underlined). The PCR products were digested with XbaI and PstI and cloned into the pMal-c2x expression vector (New England Biolabs) to create a translation fusion between the gene inserts and malE (which encodes Maltose Binding Protein [MBP]). Protein expression was induced at 0.5 $OD_{600}$ by the addition of 0.1 mM isopropyl-beta-D-thiogalactoside. Cells were harvested and resuspended in column binding buffer (20 mM Tris-HCl, pH 7.4, 200 mM NaCl, 1 mM EDTA) containing 1 mg/mL lysozyme. Cell lysate was centrifuged at 10,000×g for 10 min and the resulting supernatant was collected. Fusion protein was purified using amylose-mediated column chromatography (New England Biolabs) according to the manufacturer's instructions and examined by SDS-PAGE. Fractions containing purified fusion protein were pooled and concentrated to ~1 mg/mL using a 3 kDa centrifugal filter (MICROSEP 3K, OMEGA Pall Laboratories, Ft. Myers, Fla.). Factor Xa (New England Biolabs) was added and samples were incubated for 48 h at 21° C. Salts and buffer components were removed using a 3 kDa centrifugal filter, and protein concentration was adjusted to 1 mg/mL with the addition of sterile water.

T-Phylloplanin antibody and western blots. TI 1068 LWW was separated by SDS-PAGE and stained with Coomassie Blue. Phylloplanin III was excised and used to generate a rabbit polyclonal antibody (Strategic Biosolutions, Newark, Del.). Immunodetection was performed using a 1:10,000 dilution of phylloplanin antiserum and a 1:10,000 dilution of horseradish peroxidase-coupled anti-rabbit secondary antibody (Sigma, St. Louis, Mo.).

Protease treatment. Insoluble Proteinase K (ProtK) affixed to acrylic beads (100 mg; P0803, Sigma) was placed into mini-spin filters (732-6027, BIO-RAD). The filters containing beads were placed into empty 1.5 mL Eppendorf tubes, and the filters were washed with sterile water (700 μL; 2600×g for 1 min). The flow-through was discarded, and washing was repeated five times. The spin filters were transferred to empty 1.5 mL Eppendorf tubes. Samples were added to filters containing protease beads and incubated at 37° C. for 4 h, with periodic inversion to mix. The tubes were then centrifuged at 2600×g for 10 min, and the flow-through from each was collected and analyzed by SDS-PAGE or used in blue mold assays.

*Peronospora tabacina* spore germination and leaf infection assays. Freshly-collected *P. tabacina* spores were mixed with various concentrations of TI 1068 LWW, ProtK-treated TI 1068 LWW, or water incubated with ProtK, and germinated for 16 h in dark, humidified chambers as water drops (4 μL drops; 50 spores/μL) on microscope slides. The spores were then inspected visually at 100× magnification for germination. The absence of a germination tube after 16 h indicated inhibition. Similar experiments were performed with T-PhyllP, MBP, ProtK-treated T-PhyllP, and ProtK-treated MBP. To assess the immediacy of germination tube arrest by LWW, spores were observed after 3 h.

For the leaf infection assay, 6-wk-old, greenhouse-grown Petite Havana SR1 plants were pre-conditioned by incubation in a 21° C. growth room (14 h light) for 5 days. Dilution series (1, 5, 12.5, 25, 50, 75, 100 ng protein/μL) of TI 1068 LWW were prepared and mixed with freshly-collected *P. tabacina* spores immediately before inoculation. For each LWW dilution, 8-10 drops (4 μL drops; 100 spores/μL) were applied to one leaf of pre-conditioned plants. Plants were placed in dark, humidified chambers for 16 h to provide optimal conditions for infection, and then returned to the growth room. Treated leaves were excised 5 days after inoculation, placed in dark, humid chambers for 16 h, and then inspected for sporulation. The formation of *P. tabacina* sporulating lesions indicated successful leaf infection.

Elucidation of T-phylloplanin promoter sequence and activity. Genomic DNA was isolated from TI 1068 leaf tissue (100 mg FW) using a DNEASY plant mini kit (QIAGEN). The DNA sequence upstream of the T-Phylloplanin gene was recovered using a GENOMEWALKER kit (Clontech), according to the manufacturer's protocol. Briefly, ~4 μg genomic DNA was digested to completion (36 h) in four separate reactions with restriction enzymes that generated blunt ends (Dra I, EcoR V, Pvu II, Stu II). The resulting 'libraries' were purified by phenol/chloroform extraction and precipitation. Digested genomic DNA in each library were then ligated to 5'GenomeWalker Adaptor molecules and purified again. A primary PCR reaction for each library was performed with a sense outer adaptor primer AP1, provided in the kit, and the antisense T-Phylloplanin-specific primer (5'-TGGAACAAGTATGGCAAATGCAGCGGGG-3') (SEQ ID NO:6). Primary PCR cycling parameters were seven cycles of 25 s at 94° C. and 3 min at 72° C., followed by 32 cycles of 25 s at 94° C. and 3 min at 67° C., with a final extension of 7 min at 67° C. Products of primary PCR were diluted 1:25 and 1 μL was used in nested PCR reactions with a sense inner adaptor primer AP2, provided in the kit, and a nested antisense T-Phylloplanin-specific primer (5'-GGGGGTTGCGATTAATGCAGCCAAAAGGAAAA-3') (SEQ ID NO:7). Nested PCR cycling parameters were five cycles of 25 s at 94° C. and 3 min at 72° C., followed by 20 cycles of 25 s at 94° C. and 3 min at 67° C., with a final extension of 7 min at 67° C. A 1.8 kB product was amplified from the Stu II-based library, and gel-extracted, cloned into pGem-T, and sequenced.

PCR using a T-Phylloplanin promoter-specific sense primer (5'-TGCTCCCACCACTAGAATCACCA-3') (SEQ ID NO:12) and a T-Phylloplanin—specific antisense primer with an Xba I cut site (5'-AGCT TCTAGATGTTGGAACAAGTATGG-3' (SEQ ID NO:13); Xba I site underlined) was then used to amplify the region of *N. tabacum* genomic DNA that included the first 25 aa of the T-phylloplanin protein (which included the signal sequence), the 5' UTR, and a further 1.1 kB upstream. The PCR product was then cut with Xba I and HinD III (at a restriction site endogenous to the promoter) and cloned into the HinD III/Xba I-sites of PBIMC (kindly provided by D. Falcone, pBIMC is a variant of pBI121 modified to include a polylinker in place of the GUS gene) to replace the CaMV-35S promoter and create the vector pBI-PhylloProm. To analyze the spatial expression of the promoter, the reporter genes GUS and sGFP (kindly provided by D. Falcone) were PCR-amplified with primers that incorporated Xba I and Xho I restriction sites (GUS-sense: 5'-AGCT TCTAGAATGTTACGTCCTGTAGAAACCCCA-3' (SEQ ID NO:14); GUS-antisense: 5'-AGCT CTCGAGTCATTGTTTGCCTCCCTGCT-3' (SEQ ID NO:15); sGFP-sense: 5'-AGCT TCTAGAATGGTGAGCAAGGGCGAGGA-3' (SEQ ID NO:16); sGFP-antisense: 5'-AGCT CTCGAGGCTTTACTTGTACAGCTCGT-3' (SEQ ID NO:17); restriction sites underlined). The PCR products were gel-extracted, cut with Xba I and Xho I, and ligated between Xba I/Xho I sites in the polylinker of pBI-PhylloProm to create in-frame fusions with the T-Phylloplanin start codon and signal sequence. These constructs were transformed into *Agrobacterium tumefaciens* GV3101 by triparental mating, and introduced into TI 1068 using the leaf disk method (Horsch et al., 1985). Kanamycin-resistant plantlets were derived from kanamycin-resistant callus tissue and transferred to soil. Leaf disks from pBI-PhylloProm:GUS explants were stained for GUS activity by incubation with 0.1% X-gluc (Jefferson, 1987) and photographed. Leaf disks from pBI-PhylloProm:GFP explants were magnified and photographed using a Zeiss Axioplan-2 imaging system.

Bioinformatic analysis. Homologous open reading frames of selected cDNA or EST sequences giving significant (e-value cutoff 10e-04) BLASTn, BLASTp, and tBLASTx (Altschul et al., 1990) scores against T-Phylloplanin nucleotide and amino acid sequences were first analyzed for the presence of signal peptides using TargetP. A multiple alignment of protein sequences with the predicted signal peptides removed was performed using the CLUSTALW algorithm (DNASTAR Lasergene software, Madison, Wis.). An unrooted phylogenetic tree was constructed using the maximum parsimony algorithm PROTPARS in the PHYLIP version 3.63 software package (Felsenstein, 2004), and tree robustness was estimated with 1000 bootstrapped data sets. The tree was displayed with the TREEVIEW version 3.2 software (Page, 1996).

Sequence data from this article have been deposited with the EMBL/GenBank data libraries under accession number AY705384.

REFERENCES

Throughout this disclosure the following references have been cited and are incorporated herein:

Altschul, S. F., Gish, W., Miller, W., Myers, C. W., and Lipman, D. L. (1990). Basic local alignment search tool. J. Mol. Biol. 215, 403-410.

Curstedt, T., Jornvall, H., Robertson, B., Bergman, T., and Berggren, P. (1987). Two hydrophobic low-molecular-mass protein-fractions of pulmonary surfactant-characterization and biophysical activity. Eur. J. Biochem. 168, 255-262.

Felsenstein, J. (2004) PHYLIP (Phylogeny Inference Package) version 3.6. Distributed by the author. Department of Genome Sciences, University of Washington, Seattle.

Gallo, R. L., and Huttner, K. M. (1998). Antimicrobial peptides: an emerging concept in cutaneous biology. J. Invest. Dermatol. 111, 739-743.

Horsch, R. B., Fry, J. E., Hoffman, N. L., Eichholtz, D., Rogers, S. G., and Fraley, R. T. (1985). A simple and general method of transferring genes into plants. Science 227, 1229-1231.

Jefferson, R. A. (1987). Assaying for chimeric genes in plants: the GUS fusion system. Plant Mol. Biol. Rep. 5, 387-405.

Judd, R. C. (1994). Electrophoresis of peptides. In Basic Protein and Peptide Protocols, J. M. Walker, ed (Totowa, N.J.: Humana Press), pp. 49-57.

Kandra, L., Severson, R., and Wagner, G. J. (1990). Modified branched-chain amino-acid pathways give rise to acyl acids of sucrose esters exuded from tobacco leaf trichomes. Eur. J. Biochem. 188, 385-391.

Laemmli, U. K. (1970). Cleavage of structural proteins during the assembly of the head of bacteriophage-T4. Nature 227, 680-685.

Matsudaira, P. (1987). Sequence from picomole quantities of proteins electroblotted onto polyvinylidene difluoride membranes. J. Biol. Chem. 262, 10035-10038.

Murashige, T., and Skoog, F. (1962). A revised medium for rapid growth and bio-assays with tobacco tissue cultures. Physiol. Plant. 15, 473-497.

Page, R. D. M. (1996) TREEVIEW: an application to display phylogenetic trees on personal computers. Comp. Appl. Biosci. 12, 357-358.

Reuveni, M., Tuzun, S., Cole, J. S., Siegel, M. R., and Kuc, J. (1986). Removal of duvatrienediols from the surface of tobacco leaves increases their susceptibility to blue mold. Phytopathology 76, 1092.

Schroder, J.-M. (1999). Epithelial antimicrobial peptides: innate local host response elements. Cell. Mol. Life. Sci. 56, 32-46.

Terry, M. E., and Bonner, B. A. (1980). An examination of centrifugation as a method of extracting an extracellular solution from peas, and its use for the study of indoleacetic acid-induced growth. Plant Physiol. 66, 321-325.

Wagner, G. J., Wang, E., and Shepherd, R. W. (2004). New approaches for studying and exploiting an old protuberance, the plant trichome. Ann. Bot. (London) 93, 3-11.

Wang, E., Wang, R., DeParasis, J., Loughrin, J. H., Gan, S. S., and Wagner, G. J. (2001). Suppression of a P450 hydroxylase gene in plant trichome glands enhances natural-product-based aphid resistance. Nat. Biotechnol. 19, 371-374.

The invention claimed is:

1. A method for generating excreted gene products in a plant, said method comprising:

generating a nucleic acid fusion construct comprising a phylloplanin promoter having the nucleic acid sequence of SEQ ID NO:1 and a selected non-phylloplanin nucleic acid sequence whose transcription product is to be expressed and delivered to an aerial surface of a plant;

transfecting plant cells with the nucleic acid fusion construct resulting in plant cells stably transformed; and allowing the plant cells to regenerate into a whole plant such that cells at the aerial surface are transgenic and express a transcription product of the non-phylloplanin nucleic acid sequence, which product is excreted from the plant cells.

2. The method of claim 1, further comprising collecting the transcription product from the aerial surface of the plant.

3. The method of claim 1, wherein the transcription product confers pest resistance to the plant.

4. The method of claim 1, wherein the transcription product confers disease resistance to the plant.

5. The method of claim 1, wherein the transcription product confers improved stress resistance to the plant.

6. The method of claim 3, wherein the transcription product confers fungal resistance to the plant.

7. The method of claim 1, wherein the plant cells are from a plant species selected from the group consisting of *Medicago* sp., *Trifolium* sp., *Ulmus* sp., *Pyrus malus, Prunus armeniaca, Cynara acolymus, Asparagus officinale, Hordeum* sp., *Galium* sp., *Beta vulgaris, Prunus serotina, Vigna sinensis, Nyssa sylvatica, Quercus* sp., *Artocarpus altilis, Brassica* sp., *Andropogon scoparius, Fagopyrum sagittatum, Manihot esculenta, Apium graveolens, Agropyron deseffo-rum, Cornus florida, Phaseolus* sp., *Triticum* sp., *Oenothera caespitosa, Carya* sp., *Lactuca* sp., *Impatiens* sp., *Helianthus* sp., *Ledum decumbens, Astragalus pattersoni, Setaria italica, Vaccinium mytrillus, Avena sativa, Petroselinum crispum, Pastinaca sativa, Pisum* sp., *Prunus* sp., *Pyrus communis, Musa paradisiaca, Astragalus preussii, Raphanus sativus, Secalse cereale, Sassafras albidum, Atriplex confertifolia, Tillandsia usneoides, Spinacia oleracea, Liquidambar styraciflua, Linaria triphylla, Liriodendron tulipfera, Vicia* sp., *Citrullus vulgaris, Melilotus* sp., *Salix* sp., *Rhus copallina, Nicotiana* sp., *Vitis* sp., *Datura* sp., *Medicago* sp., *Lycopersicon* sp., *Solanum* sp., *Capsicum* sp., *Cucumis* sp., *Fragaria* sp., *Petunia* sp., *Geranium* sp., *Coleus* sp., *Stevia* sp., *Oryza* sp., *Nepeta* sp., *Zea mays, Glycine max*, and *Arabidopsis thaliana*.

8. An isolated nucleic acid sequence comprising a nucleic acid fusion construct comprising the phylloplanin promoter of SEQ ID NO:1 operably linked to a selected non-phylloplanin nucleic acid sequence.

9. The isolated nucleic acid sequence of claim 8, wherein the non-phylloplanin nucleic acid sequence encodes an amino acid sequence which is one of a pharmaceutical, cosmeceutical, or nutriceutical agent.

* * * * *

SEQUENCE LISTING

<160> NUMBER OF SEQ ID NOS: 45

<210> SEQ ID NO 1
<211> LENGTH: 1249
<212> TYPE: DNA
<213> ORGANISM: Nicotiana tabacum

<400> SEQUENCE: 1
cccattccac tatgaacttc ccggaattca attctgacta tgcgtacaag tcataatgaa 60
gctgcacata gccttcatat cgctaaacga cgtgctaggt ctcaaaacga cctgtcgggg 120
tcgttacatt agaggtgatt aacttcgtgt atacttgtgc aagtgttcta taacaatttc 180
aggccaacct agtaagagta gaaatagtga atggcacata acaaacgatc accacgaaat 240
gtacatgata taactcacac aaggtaggca cgctactaga caattaccaa taacaacaat 300
gcctaggaca tcacaagata tgaaaaatca atccttacta tcacggttga gttgtaacgt 360
gtaagaatat ttcacacttt ttagggcact aagatcactc caccaacatt tcaagagaat 420
cactggcact gccaaaaagc cctctacact gtagtgaatt tttgttagtt atctaaagtt 480
aattattcac ttagtattct ttacattagg ttcccccctt ctaggtcctg cacgtaacta 540
gattgaatgg attggtccac tctattatta cagagtaatt attaaatttt tatttgacta 600
ggcaacacta attgcactat caacaaagta ttagttctag ccttctgggt acttcatacc 660
tatgcaaatg ataattttat ttaaaacaat agatgtacat ggatataaat acctatgaaa 720
attaaataaa atataactaa gaaaaaaaat ttaaagttca ctcctaagat atcgggttat 780
tacatgacca aacacaattt gtttatcaaa tactttcaaa agaatttgtc aaacgtaaat 840
tatttttctc caaagtgact tatgaattac tatgttgata aaatactttt caaagtaact 900
aatgtttaga agtcaaggat gggcttcttt tgattattga agtttgtagc aattgtatgt 960
agttatagtc agggtgacca ccagcatctc atatagcaat acacaagtgg gttagcgtat 1020
ttgaaatttc aattagttca ttcaaatata cacgtaatag cattataagc cactttcaca 1080
acagatagat taggggtttt aaaatttcaa ccaatgatat ttactataaa ttgatcatgc 1140
acaaacctta attgagcaac acaatttctt acagcaataa ctatcacata taacaataac 1200
tgccatggct tcagcaaaaa ttttcttgat tttccttttg gctgcatta 1249

<210> SEQ ID NO 2
<211> LENGTH: 38
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(36)
<223> OTHER INFORMATION: y = c or t
<220> FEATURE:
<221> NAME/KEY: misc_feature
<222> LOCATION: (1)..(36)
<223> OTHER INFORMATION: r = a or g
<220> FEATURE:
<221> NAME/KEY: misc_feature
<222> LOCATION: (1)..(36)
<223> OTHER INFORMATION: n = Inosine
<220> FEATURE:
<221> NAME/KEY: misc_feature
<222> LOCATION: (1)..(36)
<223> OTHER INFORMATION: W= A or T

<400> SEQUENCE: 2

-continued acwttngtnt cnacwcatat ytcnggnctn gtyttttg 38

<210> SEQ ID NO 3
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(32)
<223> OTHER INFORMATION: i = inosine

<400> SEQUENCE: 3
aaraanccng tnggngcnar nccnacycta at 32

<210> SEQ ID NO 4
<211> LENGTH: 31
<212> TYPE: DNA
<213> ORGANISM: artificial
<220> FEATURE:
<223> OTHER INFORMATION: primer

<400> SEQUENCE: 4
ctcagtcccc aagtttttcc taatgcatca g 31

<210> SEQ ID NO 5
<211> LENGTH: 29
<212> TYPE: DNA
<213> ORGANISM: artificial
<220> FEATURE:
<223> OTHER INFORMATION: primer

<400> SEQUENCE: 5
ggccaagaaa gttaactagc tgatgcata 29

<210> SEQ ID NO 6
<211> LENGTH: 28
<212> TYPE: DNA
<213> ORGANISM: artificial
<220> FEATURE:
<223> OTHER INFORMATION: primer

<400> SEQUENCE: 6
tggaacaagt atggcaaatg cagcgggg 28

<210> SEQ ID NO 7
<211> LENGTH: 32
<212> TYPE: DNA
<213> ORGANISM: artificial
<220> FEATURE:
<223> OTHER INFORMATION: primer

<400> SEQUENCE: 7
gggggttgcg attaatgcag ccaaaaggaa aa 32

<210> SEQ ID NO 8
<211> LENGTH: 30
<212> TYPE: DNA
<213> ORGANISM: artificial
<220> FEATURE:
<223> OTHER INFORMATION: primer

<400> SEQUENCE: 8
agcttctaga catatttcgg ggctggtttt 30

-continued

<210> SEQ ID NO 9
<211> LENGTH: 31
<212> TYPE: DNA
<213> ORGANISM: artificial
<220> FEATURE:
<223> OTHER INFORMATION: primer

<400> SEQUENCE: 9
agctctgcag ttagccggtg ggggcgaggc c 31

<210> SEQ ID NO 10
<211> LENGTH: 27
<212> TYPE: DNA
<213> ORGANISM: artificial
<220> FEATURE:
<223> OTHER INFORMATION: primer

<400> SEQUENCE: 10
agcttctaga atacttgttc caacact 27

<210> SEQ ID NO 11
<211> LENGTH: 26
<212> TYPE: DNA
<213> ORGANISM: artificial
<220> FEATURE:
<223> OTHER INFORMATION: primer

<400> SEQUENCE: 11
agctctgcag ttaattgatg ttaaga 26

<210> SEQ ID NO 12
<211> LENGTH: 23
<212> TYPE: DNA
<213> ORGANISM: artificial
<220> FEATURE:
<223> OTHER INFORMATION: primer

<400> SEQUENCE: 12
tgctcccacc actagaatca cca 23

<210> SEQ ID NO 13
<211> LENGTH: 27
<212> TYPE: DNA
<213> ORGANISM: artificial
<220> FEATURE:
<223> OTHER INFORMATION: primer

<400> SEQUENCE: 13
agcttctaga tgttggaaca agtatgg 27

<210> SEQ ID NO 14
<211> LENGTH: 34
<212> TYPE: DNA
<213> ORGANISM: artificial
<220> FEATURE:
<223> OTHER INFORMATION: primer

<400> SEQUENCE: 14
agcttctaga atgttacgtc ctgtagaaac ccca 34

<210> SEQ ID NO 15
<211> LENGTH: 30
<212> TYPE: DNA
<213> ORGANISM: artificial
<220> FEATURE:
<223> OTHER INFORMATION: primer -continued

<400> SEQUENCE: 15
agctctcgag tcattgtttg cctccctgct 30

<210> SEQ ID NO 16
<211> LENGTH: 30
<212> TYPE: DNA
<213> ORGANISM: artificial
<220> FEATURE:
<223> OTHER INFORMATION: primer

<400> SEQUENCE: 16
agcttctaga atggtgagca agggcgagga 30

<210> SEQ ID NO 17
<211> LENGTH: 30
<212> TYPE: DNA
<213> ORGANISM: artificial
<220> FEATURE:
<223> OTHER INFORMATION: primer

<400> SEQUENCE: 17
agctctcgag gctttacttg tacagctcgt 30

<210> SEQ ID NO 18
<211> LENGTH: 15
<212> TYPE: PRT
<213> ORGANISM: Nicotiana tabacum

<400> SEQUENCE: 18

Met Ala Ser Ala Lys Ile Phe Leu Ile Phe Leu Leu Ala Ala Leu
1 5 10 15

<210> SEQ ID NO 19
<211> LENGTH: 666
<212> TYPE: DNA
<213> ORGANISM: Artificial
<220> FEATURE:
<223> OTHER INFORMATION: T-Phylloplanin cDNA

<400> SEQUENCE: 19
aacacaattt cttacagcaa taactatcac atataacaat aactgccatg gcttcagcaa 60
aaattttctt gattttcctt ttggctgcat taatcgcaac ccccgctgca tttgccatac 120
ttgttccaac acttgtttca acacatataa gtgggcttgt attttgcagc gttaacggca 180
atttagatgt catcaacgga ctcagtcccc aagtttttcc taatgcatca gtgcaattgc 240
ggtgtggagc aacaaatgtg atatcaagta caataacaaa tggatcggga gcattttcct 300
tggcggtgaa tactttccca ctgctaaact gcaatttagt ggttgcaact ccactatcaa 360
catgtaacgc gaccttacaa tcggttgggc gtttggcgtc atccttgaga cttgtaaata 420
tcactcttgg cagtggcacc ggtcttatta gagtcggttt agctcctact ggttttatac 480
ttaatcttaa catcaattaa tattgaacga gctagcctgc tggttcttaa ttagtactac 540
tactatgcat cagctsgtta actttcttgg ccagctgctt actgcaagaa taaggactgt 600
tgtttccact agtgaataaa gtgcaaatca tatttgcaag tctaaaaaaa aaaaaaaaaa 660
aaaaaa 666

<210> SEQ ID NO 20
<211> LENGTH: 150
<212> TYPE: PRT
<213> ORGANISM: Artificial

-continued

```
<220> FEATURE:
<223> OTHER INFORMATION: predicited amino acid sequence of
      T-phylloplanin cDNA

<400> SEQUENCE: 20

Met Ala Ser Ala Lys Ile Phe Leu Ile Phe Leu Leu Ala Ala Leu Ile
1               5                   10                  15

Ala Thr Pro Ala Ala Phe Ala Ile Leu Val Pro Thr Leu Val Ser Thr
            20                  25                  30

His Ile Ser Gly Leu Val Phe Cys Ser Val Asn Gly Asn Leu Asp Val
        35                  40                  45

Ile Asn Gly Leu Ser Pro Gln Val Phe Pro Asn Ala Ser Val Gln Leu
    50                  55                  60

Arg Cys Gly Ala Thr Asn Val Ile Ser Ser Thr Ile Thr Asn Gly Ser
65                  70                  75                  80

Gly Ala Phe Ser Leu Ala Val Asn Thr Phe Pro Leu Leu Asn Cys Asn
                85                  90                  95

Leu Val Val Ala Thr Pro Leu Ser Thr Cys Asn Ala Thr Leu Gln Ser
            100                 105                 110

Val Gly Arg Leu Ala Ser Ser Leu Arg Leu Val Asn Ile Thr Leu Gly
        115                 120                 125

Ser Gly Thr Gly Leu Ile Arg Val Gly Leu Ala Pro Thr Gly Phe Ile
    130                 135                 140

Leu Asn Leu Asn Ile Asn
145                 150


<210> SEQ ID NO 21
<211> LENGTH: 9
<212> TYPE: PRT
<213> ORGANISM: Nicotiana tabacum

<400> SEQUENCE: 21

Ile Leu Val Pro Thr Leu Val Ser Thr
1               5


<210> SEQ ID NO 22
<211> LENGTH: 19
<212> TYPE: PRT
<213> ORGANISM: ILVPTLVSTHISGLVFCSV

<400> SEQUENCE: 22

Ile Leu Val Pro Thr Leu Val Ser Thr His Ile Ser Gly Leu Val Phe
1               5                   10                  15

Cys Ser Val


<210> SEQ ID NO 23
<211> LENGTH: 19
<212> TYPE: PRT
<213> ORGANISM: Nicotiana tabacum

<400> SEQUENCE: 23

Ile Leu Val Pro Thr Leu Val Ser Thr His Ile Ser Gly Leu Val Phe
1               5                   10                  15

Cys Ser Val


<210> SEQ ID NO 24
<211> LENGTH: 19
<212> TYPE: PRT
<213> ORGANISM: Nicotiana tabacum
```

<400> SEQUENCE: 24

Ile Leu Val Pro Thr Leu Val Ser Thr His Ile Ser Gly Leu Val Phe
1 5 10 15

Cys Ser Val

<210> SEQ ID NO 25
<211> LENGTH: 6
<212> TYPE: PRT
<213> ORGANISM: Nicotiana tabacum

<400> SEQUENCE: 25

Ala Ser Val Gln Leu Arg
1 5

<210> SEQ ID NO 26
<211> LENGTH: 6
<212> TYPE: PRT
<213> ORGANISM: Nicotiana tabacum

<400> SEQUENCE: 26

Ile Leu Asn Leu Asn Ile
1 5

<210> SEQ ID NO 27
<211> LENGTH: 12
<212> TYPE: PRT
<213> ORGANISM: Nicotiana tabacum

<400> SEQUENCE: 27

Cys Gly Ala Thr Asn Val Ile Ser Ser Thr Ile Thr
1 5 10

<210> SEQ ID NO 28
<211> LENGTH: 18
<212> TYPE: PRT
<213> ORGANISM: Nicotiana tabacum
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (15)..(15)
<223> OTHER INFORMATION: Xaa can be any naturally occurring amino acid

<400> SEQUENCE: 28

Leu Val Val Ala Thr Pro Leu Ser Thr Cys Xaa Ala Thr Leu Xaa Ser
1 5 10 15

Val Gly

<210> SEQ ID NO 29
<211> LENGTH: 6
<212> TYPE: PRT
<213> ORGANISM: Nicotiana tabacum

<400> SEQUENCE: 29

Ile Leu Asn Leu Asn Ile
1 5

<210> SEQ ID NO 30
<211> LENGTH: 12
<212> TYPE: PRT
<213> ORGANISM: Nicotiana tabacum
<220> FEATURE:
<221> NAME/KEY: misc_feature -continued
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 30

```
Cys Gly Ala Thr Xaa Val Xaa Ser Ser Thr Ile Thr
1               5                   10
```

<210> SEQ ID NO 31
<211> LENGTH: 9
<212> TYPE: PRT
<213> ORGANISM: Nicotiana tabacum

<400> SEQUENCE: 31

```
Ile Arg Val Gly Leu Ala Pro Thr Gly
1               5
```

<210> SEQ ID NO 32
<211> LENGTH: 127
<212> TYPE: PRT
<213> ORGANISM: Nicotiana sp.

<400> SEQUENCE: 32

```
Ile Leu Val Pro Thr Leu Val Ser Thr His Ile Ser Gly Leu Val Phe
1               5                   10                  15

Cys Ser Val Asn Gly Asn Leu Asp Val Ile Asn Gly Leu Ser Pro Gln
            20                  25                  30

Val Phe Pro Asn Ala Ser Val Gln Leu Arg Cys Gly Ala Thr Asn Val
        35                  40                  45

Ile Ser Ser Thr Ile Thr Asn Gly Ser Gly Ala Phe Ser Leu Ala Val
    50                  55                  60

Asn Thr Phe Pro Leu Leu Asn Cys Asn Leu Val Val Ala Thr Pro Leu
65                  70                  75                  80

Ser Thr Cys Asn Ala Thr Leu Gln Ser Val Gly Arg Leu Ala Ser Ser
                85                  90                  95

Leu Arg Leu Val Asn Ile Thr Leu Gly Ser Gly Thr Gly Leu Ile Arg
            100                 105                 110

Val Gly Leu Ala Pro Thr Gly Phe Ile Leu Asn Leu Asn Ile Asn
        115                 120                 125
```

<210> SEQ ID NO 33
<211> LENGTH: 145
<212> TYPE: PRT
<213> ORGANISM: Nicotiana sp.

<400> SEQUENCE: 33

```
Gln Ile Leu Pro Pro Pro Ile Leu Pro Pro Thr Ile Ile Arg Pro Pro
1               5                   10                  15

Pro Ile Leu Pro Pro Ile Val Leu Pro Pro Pro Ile Val Leu Asn Pro
            20                  25                  30

Val Leu Asn Val Thr Gly Ile Val Ser Cys Ser Val Asn Ala Thr Val
        35                  40                  45

Asn Thr Thr Thr Ala Pro Pro Phe Pro Asn Ala Gln Val Gln Leu Arg
    50                  55                  60

Cys Gly Gly Leu Val Val Gly Ala Ala Thr Thr Asn Gln Ser Gly Ala
65                  70                  75                  80

Phe Asn Ile Val Val Asn Pro Phe Leu Ser Thr Val Ala Asn Leu Leu
```

-continued

```
                85                  90                  95

Ser Cys Arg Val Val Val Thr Thr Pro Leu Ala Thr Cys Asn Val Thr
            100                 105                 110

Leu Pro Ser Thr Gly Thr Leu Gln Ala Pro Leu Gln Ile Val Gly Asn
        115                 120                 125

Ile Leu Asn Ile Leu Phe Ala Ile Pro Gly Gln Phe Leu Tyr Leu Gln
    130                 135                 140

Val
145


<210> SEQ ID NO 34
<211> LENGTH: 142
<212> TYPE: PRT
<213> ORGANISM: Nicotiana sp.

<400> SEQUENCE: 34

Gln Leu Gly Gly Leu Gly Gly Gly Leu Gly Gly Leu Gly Met Leu Leu
1               5                   10                  15

Gly Gly Leu Thr Asn Ile Phe Asn Ile Gln Gly Leu Leu Met Cys Ser
            20                  25                  30

Val Thr Gly Thr Val Ser Thr Asn Asn Ala Thr Ala Val Pro Pro Phe
        35                  40                  45

Pro Asn Ala Gly Ile Val Phe Gln Cys Thr Gly Gln Asn Val Ser Ser
    50                  55                  60

Thr Thr Thr Asn Ala Asn Gly Val Phe Ser Ile Pro Thr Ile Gly Leu
65                  70                  75                  80

Pro Phe Ser Pro Ser Thr Leu Leu Ser Ser Gly Cys Arg Leu Val Val
                85                  90                  95

Thr Thr Pro Leu Thr Ala Cys Asn Val Ser Leu Pro Ala Ala Gly Leu
            100                 105                 110

Leu Met Ala Pro Leu Ser Leu Val Gly Thr Ala Ala Gly Asp Gly Leu
        115                 120                 125

Asn Ile Phe Ser Leu Val Pro Ser Ala Phe Gly Leu Val Gly
    130                 135                 140


<210> SEQ ID NO 35
<211> LENGTH: 132
<212> TYPE: PRT
<213> ORGANISM: Nicotiana sp.

<400> SEQUENCE: 35

Val Leu Ile Ala Ala Gln Ala Asp Glu Ala Gln Gly Leu Pro Pro Ile
1               5                   10                  15

Thr Ala Ala Val Asn Ile Ser Gly Ile Val Thr Cys Ser Val Asn Gly
            20                  25                  30

Ser Ala Asn Ala Pro Pro Phe Ala Asn Ala Leu Val Glu Leu Ser Cys
        35                  40                  45

Gly Gly Asn Val Ile Ala Ser Ala Val Thr Asn Ala Gln Gly Val Phe
    50                  55                  60

Asn Ile Thr Val Asn Pro Leu Arg Val Thr Leu Asn Asn Leu Leu Ser
65                  70                  75                  80

Ser Cys Arg Ile Ile Val Ala Thr Pro Leu Ser Asn Cys Asn Ala Thr
                85                  90                  95

Leu Pro Thr Ala Gly Thr Leu Gln Ser Ala Leu Gln Val Ala Gly Thr
            100                 105                 110

Phe Ile Arg Gly Ile Leu Asn Asn Val Asn Leu Val Pro Ile Arg Phe
```

-continued

```
        115                 120                 125

Arg Leu Val Val
    130


<210> SEQ ID NO 36
<211> LENGTH: 153
<212> TYPE: PRT
<213> ORGANISM: Nicotiana sp.

<400> SEQUENCE: 36

Gln Leu Gly Leu Gly Gly Ser Gly Gly Leu Gly Gly Leu Ile Gly Gly
1               5                   10                  15

Leu Val Gly Gly Leu Gly Gly Leu Val Gly Gly Leu Val Gly Gly Ile
            20                  25                  30

Leu Asn Leu Val Asn Ile Asn Gly Val Val Phe Cys Ser Leu Asn Gly
        35                  40                  45

Ala Pro Ser Gly Thr Ser Thr Pro Ala Phe Ala Asn Ala Gly Val Glu
    50                  55                  60

Leu Gln Cys Gly Arg Gln Asn Arg Val Val Ser Thr Ala Thr Thr Asn
65                  70                  75                  80

Ala Ala Gly Leu Phe Ser Leu Pro Thr Asp Ser Ile Gln Met Leu Leu
                85                  90                  95

Ser Thr Leu Leu Ser Asp Cys Arg Val Val Val Thr Thr Pro Leu Ser
            100                 105                 110

Thr Cys Asn Ala Asn Leu Pro Ser Val Gly Asn Leu Val Ser Arg Leu
        115                 120                 125

Ala Met Ile Gly Asn Ser Leu Thr Gly Leu Leu Asn Ile Ile Ser Ile
    130                 135                 140

Ile Pro Ala Gly Phe Gly Leu Leu Asn
145                 150


<210> SEQ ID NO 37
<211> LENGTH: 128
<212> TYPE: PRT
<213> ORGANISM: Nicotiana sp.

<400> SEQUENCE: 37

Gln Ser Gly Leu Gly Gly Ile Asn Val Pro Ile Ile Asn Gly Val Leu
1               5                   10                  15

Phe Cys Thr Ile Asn Gly Ala Pro Leu Asn Gly Thr Pro Ala Pro Ala
            20                  25                  30

Phe Ala Asn Ala Val Val Gln Leu Gln Cys Gly Asn Leu Asn Arg Val
        35                  40                  45

Val Ala Glu Thr Ile Thr Asn Ile Ala Gly Leu Phe Thr Phe Ser Thr
    50                  55                  60

Asn Gly Ile Gln Ile Ser Leu Pro Thr Leu Leu Asn Asp Cys Arg Ile
65                  70                  75                  80

Val Val Pro Thr Pro Arg Ser Ser Cys Asp Ala Thr Leu Pro Ser Thr
                85                  90                  95

Gly Gln Leu Ile Ser Gln Leu Asn Leu Val Gly Ser Ile Val Ser Gly
            100                 105                 110

Leu Leu Asn Ile Val Ala Ile Leu Pro Thr Gly Phe Ile Pro Thr Ile
        115                 120                 125


<210> SEQ ID NO 38
<211> LENGTH: 124
<212> TYPE: PRT
```

-continued

<213> ORGANISM: Nicotiana sp.

<400> SEQUENCE: 38

Ala Pro Pro Ala Gln Pro Pro Arg Ile Gln Ala Asp Val Val Val Met
1 5 10 15

Gly Tyr Val Pro Cys Asn Asn Gly Thr Ser Met Lys Ser Gly Ser Ala
20 25 30

Pro Gly Phe Pro Asn Ala Val Val Gln Leu Gln Cys Ala Gly Asp Ala
35 40 45

Val Ala Ala Val Ala Ala Gly Ser Ala Thr Thr Asp Gly Lys Gly Trp
50 55 60

Phe Arg Met Ala Met Asn Thr Thr Ala Ala Leu Ser Ser Val Ala Ser
65 70 75 80

Gly Cys Ser Leu Val Val Thr Thr Pro Leu Ala Thr Cys Asp Ala Ala
85 90 95

Leu Pro Ala Thr Gly Thr Leu Gln Ser Gly Leu Arg Leu Leu Val Ser
100 105 110

Met Val Phe Phe Pro Arg Gly Phe Ser Tyr Val Val
115 120

<210> SEQ ID NO 39
<211> LENGTH: 118
<212> TYPE: PRT
<213> ORGANISM: Nicotiana sp.

<400> SEQUENCE: 39

Lys Leu Gly Arg Leu Val Val Thr Gly Val Val Pro Cys Asn Thr Gly
1 5 10 15

Ser Leu Ile Asp Ile Ala Thr Ser Pro Ala Phe Pro Asn Ala Asp Val
20 25 30

Glu Leu Arg Cys Ala Gly Lys Leu Val Ala Gly Ala Thr Thr Asn Ser
35 40 45

Asn Gly Ser Phe Ala Met Glu Ala Asp Leu Thr Ser Gly Leu Ala Met
50 55 60

Leu Ile Gly Gly Cys Lys Leu Val Val Asp Thr Pro Leu Ile Lys Cys
65 70 75 80

Asp Ala Asn Leu Pro Ala Ala Gly Ser Leu Val Ser Tyr Leu Gln Gly
85 90 95

Pro Leu Thr Arg Leu Leu Gly Gly Ile Phe Arg Leu Phe Pro Ala Gly
100 105 110

Phe Ser Phe His Ala His
115

<210> SEQ ID NO 40
<211> LENGTH: 132
<212> TYPE: PRT
<213> ORGANISM: Nicotiana sp.

<400> SEQUENCE: 40

Gln Leu Gly Gly Leu Leu Gly Gly Leu Leu Gly Pro Ile Ser Ile Asp
1 5 10 15

Gly Val Leu Phe Cys Ser Leu Asn Gly Lys Ile Asp Val Leu Asn Gly
20 25 30

Ala Thr Thr Pro Ile Phe Pro Asn Ala Ser Val Gln Leu Arg Cys Gly
35 40 45

Ala Gly Asn Val Val Ser Ser Thr Thr Thr Asn Gly Ser Gly Ala Phe
50 55 60

-continued

Ser Leu Val Leu Asn Pro Val Gln Asn Ile Leu Ser Ser Leu Leu Ser
65 70 75 80

Asn Cys Asn Ile Val Val Thr Thr Pro Leu Ser Thr Cys Asn Ala Ser
85 90 95

Leu Pro Ser Val Gly Val Leu Gln Ala Pro Leu Gln Ile Val Gly Arg
100 105 110

Thr Thr Gly Gly Leu Val Asn Leu Val Thr Gly Val Phe Gln Leu Ile
115 120 125

Pro Leu Leu Asn
130

<210> SEQ ID NO 41
<211> LENGTH: 133
<212> TYPE: PRT
<213> ORGANISM: Nicotiana sp.

<400> SEQUENCE: 41

Gln Leu Gly Gly Leu Leu Gly Gly Leu Leu Ala Pro Thr Ser Ile Glu
1 5 10 15

Gly Val Leu Phe Cys Ser Leu Asn Gly Lys Ile Asp Val Leu Asn Gly
20 25 30

Ala Thr Thr Pro Ile Phe Pro Asp Ala Ser Val Gln Leu Arg Cys Gly
35 40 45

Ala Gly Asn Val Val Ser Ser Thr Thr Thr Asn Gly Ser Gly Ala Phe
50 55 60

Ser Leu Val Thr Ser Pro Val Gln Ser Leu Leu Ser Ser Leu Leu Ser
65 70 75 80

Asp Cys Asn Ile Val Val Thr Thr Pro Leu Ser Thr Cys Asn Ala Thr
85 90 95

Leu Pro Ser Val Gly Val Leu Gln Ala Pro Leu Gln Ile Val Gly Lys
100 105 110

Thr Ala Gly Gly Gly Leu Leu Asn Ile Val Lys Leu Val Thr Gly Ala
115 120 125

Phe Gln Leu Ile Asn
130

<210> SEQ ID NO 42
<211> LENGTH: 115
<212> TYPE: PRT
<213> ORGANISM: Nicotiana sp.

<400> SEQUENCE: 42

Cys Thr Pro Asn Gly Asn Ile Gly Val Asn Gly Thr Ser Thr Pro Val
1 5 10 15

Phe Pro Asn Ala Ala Val Gln Leu Gln Cys Gly Gly Thr Val Val Ser
20 25 30

Thr Thr Thr Thr Asn Gly Leu Gly Gln Phe Ser Met Leu Leu Asp Pro
35 40 45

Leu Asn Phe Val Leu Ser Thr Leu Val Ser Gly Cys Arg Leu Ala Val
50 55 60

Thr Thr Pro Leu Ala Thr Cys Asn Ala Ser Leu Pro Ser Ala Gly Gly
65 70 75 80

Leu Ile Ser Thr Leu Gln Phe Val Gly Ser Thr Val Leu Gly Leu Leu
85 90 95

Asn Val Gly Asn Ile Ile Pro Ser Gly Phe Asn Phe Ser Ala Asn Met
100 105 110

-continued

```
Asn Leu Asn
        115


<210> SEQ ID NO 43
<211> LENGTH: 138
<212> TYPE: PRT
<213> ORGANISM: Nicotiana sp.

<400> SEQUENCE: 43

Ala Pro Val Ala Glu Ala Gln Leu Gly Leu Ile Gly Gly Leu Leu Gly
1               5                   10                  15

Leu Ile Arg Ile Gln Gly Thr Leu Phe Cys Thr Ala Asp Gly Asn Ile
            20                  25                  30

Gly Ala Asn Gly Thr Ala Thr Pro Val Phe Pro Asn Ala Leu Val Gln
        35                  40                  45

Leu Gln Cys Gly Gly Asn Val Val Ser Thr Ser Thr Thr Asn Gly Ser
    50                  55                  60

Gly Met Phe Ser Ile Leu Leu Asp Pro Leu Ser Tyr Ile Leu Ser Ser
65                  70                  75                  80

Ile Leu Ser Asp Cys Asn Leu Lys Val Asp Thr Pro Leu Ile Ser Cys
                85                  90                  95

Asn Ser Ser Leu Pro Ala Val Gly Gly Leu Leu Ser Pro Leu Arg Phe
            100                 105                 110

Ile Gly Asn Thr Ala Leu Gly Ala Val Leu Ser Val Ala Asn Ile Ile
        115                 120                 125

Pro Ala Gly Phe Arg Phe Val Pro Ser Asn
    130                 135


<210> SEQ ID NO 44
<211> LENGTH: 132
<212> TYPE: PRT
<213> ORGANISM: Nicotiana sp.

<400> SEQUENCE: 44

Gln Leu Gly Ile Leu Ser Gly Leu Leu Gly Ser Val Ser Asn Ile Gln
1               5                   10                  15

Gly Thr Val Phe Cys Thr Ser Lys Asp Asn Met Gly Val Lys Gly Ala
            20                  25                  30

Ser Val Pro Val Phe Pro Asn Ala Gln Val Gln Leu Val Cys Gly Gly
        35                  40                  45

Lys Glu Leu Ser Asn Ala Lys Thr Asn Asp Asp Gly Thr Phe Ser Met
    50                  55                  60

Met Met Asp Pro Leu Leu Leu Asp Leu Ala Ser Leu Leu Ser Gly Cys
65                  70                  75                  80

Asn Leu Val Val Ala Thr Pro Leu Ser Asn Cys Asn Ala Lys Leu Pro
                85                  90                  95

Ser Thr Gly Gly Leu Ile Ser Thr Leu Asn Phe Ala Gly Ile Thr Ser
            100                 105                 110

Val Gly Thr Gln Thr Met Ala Asn Ile Ile Pro Ser Gly Phe His Phe
        115                 120                 125

Leu Pro Ser Ile
    130


<210> SEQ ID NO 45
<211> LENGTH: 118
<212> TYPE: PRT
<213> ORGANISM: Nicotiana sp.
```

-continued

```
<400> SEQUENCE: 45

Lys Leu Gly Arg Leu Val Val Ser Gly Val Ala Pro Cys Asn Thr Gly
1               5                   10                  15

Ser Leu Ile Asp Ile Ala Thr Ser Pro Ala Phe Pro Asn Ala Glu Val
            20                  25                  30

Glu Leu Arg Cys Ala Gly Gln Val Val Ala Gly Ala Thr Thr Asn Thr
        35                  40                  45

Asn Gly Ser Phe Thr Met Glu Ala Asp Leu Thr Ser Ala Leu Ala Ala
    50                  55                  60

Phe Ile Gly Arg Cys Ser Leu Val Val Asp Thr Pro Leu Ile Lys Cys
65                  70                  75                  80

Asp Ala Gln Leu Pro Pro Ala Gly Arg Leu Val Ser Tyr Leu Gln Gly
                85                  90                  95

Pro Leu Thr Arg Leu Leu Gly Gly Ile Phe His Leu Phe Pro Ala Gly
            100                 105                 110

Phe Ser Phe His Ser Arg
        115
```